(12) United States Patent
Takeuchi et al.

(10) Patent No.: US 11,432,725 B2
(45) Date of Patent: Sep. 6, 2022

(54) OPTICAL PROBE AND ASSEMBLY THEREOF HAVING SPECIFIC OPTICAL COMPONENT ADHESIVE CONFIGURATION

(71) Applicant: Go!Foton Holdings, Inc., Somerset, NJ (US)

(72) Inventors: Kenichiro Takeuchi, North Brunswick, NJ (US); Akimitsu Sato, Somerset, NJ (US)

(73) Assignee: Go!Foton Holdings, Inc., Somerset, NJ (US)

( * ) Notice: Subject to any disclaimer, the term of this patent is extended or adjusted under 35 U.S.C. 154(b) by 0 days.

(21) Appl. No.: 16/802,138

(22) Filed: Feb. 26, 2020

(65) Prior Publication Data

US 2020/0187781 A1 Jun. 18, 2020

Related U.S. Application Data

(62) Division of application No. 15/872,625, filed on Jan. 16, 2018, now Pat. No. 10,631,733.

(Continued)

(51) Int. Cl.
*A61B 5/00* (2006.01)
*A61B 5/02* (2006.01)
(Continued)

(52) U.S. Cl.
CPC ........ *A61B 5/0084* (2013.01); *A61B 5/02007* (2013.01); *G02B 6/262* (2013.01);
(Continued)

(58) Field of Classification Search
CPC .............. A61B 5/0084; A61B 5/02007; A61B 2562/0233; A61B 2090/3614;
(Continued)

(56) References Cited

U.S. PATENT DOCUMENTS 2,111,972 A 3/1938 Koch
3,556,085 A * 1/1971 Takahashi .......... A61B 1/00165
600/129

(Continued)

FOREIGN PATENT DOCUMENTS

CN 102667559 A 9/2012
EP 0062484 A1 10/1982
(Continued)

OTHER PUBLICATIONS

Reference number list for the present application of U.S. Appl. No. 16/802,138 (Year: 2021).*

(Continued)

*Primary Examiner* — Andrew Jordan
(74) *Attorney, Agent, or Firm* — Lerner, David, Littenberg, Krumholz & Mentlik, LLP

(57) ABSTRACT

An optical probe includes a lens combination, an optical fiber assembly, and a cover. The lens combination includes a first lens and a second lens. The first lens has a generally planar first lens surface defining an oval edge. The second lens has a generally planar second lens surface operatively coupled to the first lens surface. The second lens has four primary edges and at least two secondary edges connecting pairs of the primary edges. Each primary edge extends in substantially a straight line between two spaced-apart points at the oval edge of the first lens. The optical fiber and the lens combination are configured such that a light beam exiting the optical fiber enters the lens combination at an entering surface of the first lens, passes through the first lens and exits the first lens at the first lens surface. The cover circumferentially surrounds the optical fiber assembly.

22 Claims, 11 Drawing Sheets

Related U.S. Application Data

(60) Provisional application No. 62/470,693, filed on Mar. 13, 2017.

(51) Int. Cl.
*G02B 23/24* (2006.01)
*G02B 6/26* (2006.01)
*G02B 23/26* (2006.01)
G02B 3/00 (2006.01)
A61B 90/00 (2016.01)
G02B 27/09 (2006.01)
G02B 27/30 (2006.01)

(52) U.S. Cl.
CPC ....... *G02B 23/243* (2013.01); *G02B 23/2469* (2013.01); *G02B 23/26* (2013.01); *A61B 2090/3614* (2016.02); *A61B 2562/0233* (2013.01); *G02B 3/0087* (2013.01); *G02B 27/0955* (2013.01); *G02B 27/30* (2013.01)

(58) Field of Classification Search
CPC .. G02B 23/2469; G02B 23/26; G02B 23/243; G02B 6/262; G02B 27/0955; G02B 27/30; G02B 27/0025; G02B 27/0966; G02B 3/0087; G02B 19/0028
See application file for complete search history.

(56) References Cited

U.S. PATENT DOCUMENTS

| | | | |
|---|---|---|---|
| 3,736,060 A | 5/1973 | Mayo | |
| 3,753,610 A | 8/1973 | Samuel | |
| 3,761,106 A | 9/1973 | Schwarz | |
| 4,173,394 A | 11/1979 | Clave et al. | |
| 4,251,158 A | 2/1981 | Kimura | |
| 4,403,824 A | 9/1983 | Scott | |
| 4,406,520 A | 9/1983 | Sato | |
| 4,446,768 A | 5/1984 | Sirmans | |
| 4,544,843 A | 10/1985 | Kern et al. | |
| 4,703,332 A | 10/1987 | Crotti et al. | |
| 5,006,020 A | 4/1991 | Roos | |
| 5,007,220 A | 4/1991 | Lalvani | |
| 5,028,127 A | 7/1991 | Spitzberg | |
| 5,223,983 A | 6/1993 | Oono et al. | |
| 5,251,633 A * | 10/1993 | Wunderling | A61B 5/1459 600/311 |
| 5,265,395 A | 11/1993 | Lalvani | |
| 5,331,622 A | 7/1994 | Ernst et al. | |
| 5,440,126 A | 8/1995 | Kemsley | |
| 5,539,422 A | 7/1996 | Heacock et al. | |
| 5,768,024 A | 6/1998 | Takahashi | |
| 5,774,608 A | 6/1998 | Allen et al. | |
| 5,812,713 A | 9/1998 | Allen et al. | |
| 5,847,878 A | 12/1998 | Fogino | |
| 5,861,995 A | 1/1999 | Fogino | |
| 5,938,566 A | 8/1999 | Rodriguez-Ferre | |
| 6,055,110 A | 4/2000 | Kintz et al. | |
| 6,278,556 B1 | 8/2001 | Togino | |
| 6,324,363 B1 | 11/2001 | Watanabe et al. | |
| 6,445,939 B1 | 9/2002 | Swanson et al. | |
| 6,671,461 B2 | 12/2003 | Tochigi | |
| 6,731,355 B2 | 5/2004 | Miyashita | |
| 6,763,626 B1 | 7/2004 | Wieringa | |
| 6,791,638 B2 | 9/2004 | Miyashita et al. | |
| 6,928,843 B1 | 8/2005 | Pimie | |
| 6,956,995 B1 | 10/2005 | Shafaat et al. | |
| 7,019,909 B2 | 3/2006 | Yamazaki et al. | |
| 7,113,349 B2 | 9/2006 | Takahashi | |
| 7,123,425 B2 | 10/2006 | Kuba | |
| 7,215,455 B2 | 5/2007 | Matsuoka | |
| 7,436,599 B2 | 10/2008 | Mihara et al. | |
| 7,515,345 B2 | 4/2009 | Heimer | |
| 7,611,105 B1 | 11/2009 | Carazo | |
| 7,692,170 B2 | 4/2010 | Gaus et al. | |
| 7,715,105 B2 | 5/2010 | Forkey et al. | |
| 7,872,806 B2 | 1/2011 | Mihara et al. | |
| 7,952,718 B2 * | 5/2011 | Li | G01B 9/02091 356/479 |
| 7,978,255 B2 | 7/2011 | Suzuki | |
| 7,988,622 B2 | 8/2011 | Achas Gandarias | |
| 8,380,037 B2 | 2/2013 | Maruyama et al. | |
| 8,726,539 B2 | 5/2014 | Potter et al. | |
| 8,863,957 B2 | 10/2014 | Kusuhara et al. | |
| 9,069,115 B2 | 6/2015 | Jupta et al. | |
| 9,069,122 B2 | 6/2015 | Takeuchi et al. | |
| 9,229,476 B2 | 1/2016 | Yanev et al. | |
| 9,383,495 B2 | 7/2016 | Maruyama et al. | |
| 9,441,967 B2 | 9/2016 | Ranieri et al. | |
| 9,527,220 B1 | 12/2016 | Drouillard | |
| 10,234,676 B1 * | 3/2019 | Elmaanaoui | G02B 23/2446 |
| 10,561,303 B2 * | 2/2020 | Wu | A61B 1/00188 |
| 10,606,064 B2 * | 3/2020 | Wu | A61B 1/043 |
| 10,631,733 B2 * | 4/2020 | Takeuchi | A61B 5/0084 |
| 10,791,923 B2 * | 10/2020 | Wu | G02B 6/262 |
| 10,806,329 B2 * | 10/2020 | Elmaanaoui | A61B 1/00188 |
| 10,816,789 B2 * | 10/2020 | Elmaanaoui | A61B 1/043 |
| 2002/0015563 A1 * | 2/2002 | Murakami | G02B 6/43 385/53 |
| 2002/0030901 A1 | 3/2002 | Kobayashi et al. | |
| 2003/0004412 A1 | 1/2003 | Izatt et al. | |
| 2003/0169584 A1 | 9/2003 | Miyashita | |
| 2003/0169586 A1 | 9/2003 | Miyashita et al. | |
| 2005/0001082 A1 | 1/2005 | Strauss et al. | |
| 2005/0128604 A1 | 6/2005 | Kuba | |
| 2005/0220420 A1 * | 10/2005 | Sasaki | G02B 6/3825 385/55 |
| 2006/0067620 A1 | 3/2006 | Shishkov et al. | |
| 2007/0214986 A1 | 9/2007 | Gaus et al. | |
| 2008/0074754 A1 | 3/2008 | Sakamoto | |
| 2009/0002857 A1 | 1/2009 | Tokunaga et al. | |
| 2009/0122171 A1 | 5/2009 | Suzuki | |
| 2009/0190883 A1 | 7/2009 | Kato et al. | |
| 2009/0323076 A1 * | 12/2009 | Li | A61B 5/0066 356/479 |
| 2010/0024244 A1 | 2/2010 | Potter | |
| 2010/0053849 A1 | 3/2010 | Poltorak et al. | |
| 2010/0168521 A1 | 7/2010 | Acha Gandarias et al. | |
| 2010/0282626 A1 | 11/2010 | Bertuzzi et al. | |
| 2011/0049764 A1 | 3/2011 | Lee et al. | |
| 2011/0137124 A1 | 6/2011 | Milner et al. | |
| 2011/0286115 A1 | 11/2011 | Nagaoka et al. | |
| 2012/0006726 A1 | 1/2012 | Kusuhara et al. | |
| 2012/0069861 A1 | 3/2012 | Neuberger | |
| 2012/0243251 A1 | 9/2012 | Suzuki et al. | |
| 2013/0070255 A1 | 3/2013 | Nagai | |
| 2014/0075776 A1 | 3/2014 | Potter et al. | |
| 2014/0104706 A1 | 4/2014 | Takeuchi et al. | |
| 2014/0333543 A1 | 11/2014 | Yanev et al. | |
| 2014/0352161 A1 | 12/2014 | Ranieri et al. | |
| 2015/0004741 A1 | 1/2015 | Kusuhara et al. | |
| 2015/0025369 A1 | 1/2015 | Bhagavatula et al. | |
| 2015/0309217 A1 | 10/2015 | Castro et al. | |
| 2016/0018581 A1 | 1/2016 | Maruyama et al. | |
| 2016/0227990 A1 * | 8/2016 | Li | A61B 1/00172 |
| 2017/0238807 A9 * | 8/2017 | Vertikov | A61B 5/0066 |
| 2017/0245747 A1 * | 8/2017 | Soudagar | A61B 1/055 |
| 2017/0274966 A1 | 9/2017 | Boonlikitcheva | |
| 2018/0256032 A1 | 9/2018 | Takeuchi et al. | |
| 2018/0296074 A1 * | 10/2018 | Trulson | G02B 21/361 |
| 2018/0358170 A1 | 12/2018 | Hirabayashi et al. | |
| 2018/0358172 A1 | 12/2018 | Yamamoto et al. | |
| 2019/0027294 A1 | 1/2019 | Yoshikawa et al. | |
| 2019/0038983 A1 | 2/2019 | Matos | |
| 2019/0223699 A1 * | 7/2019 | Wu | A61B 5/0071 |
| 2019/0227297 A1 * | 7/2019 | Wu | G01B 11/2441 |
| 2020/0187781 A1 * | 6/2020 | Takeuchi | A61B 5/02007 |

FOREIGN PATENT DOCUMENTS

| | | |
|---|---|---|
| JP | H0640734 A | 2/1994 |
| JP | H10268159 A | 10/1998 |
| JP | H1156786 A | 3/1999 |

(56) References Cited

FOREIGN PATENT DOCUMENTS

| JP | H11262467 | A | 9/1999 |
|---|---|---|---|
| JP | 2001170850 | A | 6/2001 |
| JP | 2004223269 | A | 8/2004 |
| JP | 2008514383 | A | 5/2008 |
| JP | 2009087462 | A | 4/2009 |
| JP | 2009178229 | A | 8/2009 |
| JP | 2013141499 | A | 7/2013 |
| JP | 2017046882 | A | 3/2017 |
| JP | 2017047186 | A | 3/2017 |
| WO | 2011062087 | A1 | 5/2011 |
| WO | 2011074051 | A1 | 6/2011 |
| WO | 2011132664 | A1 | 10/2011 |

OTHER PUBLICATIONS

Reference number list for U.S. Patent Application Publication No. 2014/0104706 of Takeuchi et al. (Takeuchi, cited by Applicant) (Year: 2021).*
Reference number list for U.S. Patent Application Publication No. 2016/0227990 of Li et al. (Li) (Year: 2021).*
Lindsey Thompson, "University of Nebraska 1—Lincoln DigitalCommons@University of Nebraska—Lincoln MAT Exam Expository Papers Math in the Middle Institute Partnership Perimeter and Area of Inscribed and Circumscribed Polygons", Jan. 1, 2007 (Jan. 1, 2007), XP055492484, Retrieved from the Internet: URL: https://digitalconmons.unl.edu/cgi/viewcontent.cgi?article=1042&context=mathmide xppap [retrieved on Jul. 13, 2018]* the whole document*.
Extended European Search Report and Written Opinion for EP Application No. 18161608.7, dated Jul. 24, 2018.
Partial International Search Report for Application No. PCT/US2013/064282 dated Dec. 19, 2013.
International Search Report and Written Opinion for Application No. PCT/US2013/064282 dated Feb. 21, 2014.
Chinese Search Report for Application No. 201810201246.3, dated Oct. 13, 2020, pp. 1-2.
Japanese Search Report for Application No. 2020045989, dated Mar. 9, 2021, 6 pages.
Search Report from 3rd Chinese Office Action for Application No. 2018102012463 dated Mar. 30, 2021; 2 pages.

* cited by examiner

OPTICAL PROBE AND ASSEMBLY THEREOF HAVING SPECIFIC OPTICAL COMPONENT ADHESIVE CONFIGURATION

CROSS-REFERENCE TO RELATED APPLICATIONS

The present application is a divisional of U.S. patent application Ser. No. 15/872,625, filed Jan. 16, 2018, which claims the benefit of U.S. Provisional Application No. 62/470,693, filed Mar. 13, 2017, and is related to U.S. Pat. No. 9,069,122 filed Mar. 13, 2013, and U.S. Provisional Application No. 61/849,819 filed Oct. 12, 2012, the disclosures of which are hereby incorporated by reference herein.

FIELD

The present disclosure generally relates to optical devices and systems, and methods of their manufacture. In particular, the present disclosure relates to compensating for astigmatism caused by an optical component of an optical device and system as well as to assemblies for providing optical sensing functions and illumination within internal structures.

BACKGROUND

Optical devices and systems often are used to route an optical signal therethrough, and emit the optical signal so that the emitted optical signal is directed towards a target. For example, an optical device may be used to route light supplied from an optical fiber through several optical components, such as lenses and other transparent elements, for example, transparent glass or plastic tubes, of the device, before emitting the light so the emitted light is focused at a predetermined location external to the device.

In an optical device, the optical properties of optical components through which light is passed or which reflect or refract light may determine transmission characteristics of the light emitted from the optical device. As is well known, light is composed of bundles of rays traveling in two planes, known as tangential and sagittal planes, that are orthogonal to each other. When light travels through an optical component of the optical device, the optical properties and geometry of the outer surfaces of the optical component may cause the two planes of rays of the light emitted from the optical component to have different focal lines or points, which is a condition known as astigmatism.

An optical device often includes an optical component to compensate for astigmatism expected to be caused by another optical component of the device, such that the two planes of rays constituting the light emitted from the optical device may be focused at a same focal point or line. For example, an optical probe that operates to emit light having a focus line or beam waist at a target location external to the probe sometimes includes a transparent tube through which the light is emitted from the probe. The tube of the probe acts as an optical lens that causes astigmatism in the light passing therethrough. The optical probe, therefore, includes another optical component, such as an optical prism, through which the light passes before the light passes through the tube, and which causes astigmatism in the light that compensates for the astigmatism expected to be caused by the tube. The astigmatism caused by the other optical component, thus, provides for the desirable condition that the light emitted from the optical probe has minimal or no astigmatism.

A continuing need exists for an optical component that may compensate for astigmatism caused by another optical component in an optical device and where the optical component can be manufactured with relative ease and at low cost.

BRIEF SUMMARY

A method of manufacturing an optical component may include: providing a plate formed from a transparent material, the plate having a planar surface and a depth, cutting depth-wise through the planar surface of the plate along first and second linear directions to define first and second planar surfaces, and cutting depth-wise through the planar surface of the plate along a curved direction to define a curved surface such that an optical component is obtained including the first and second planar surfaces and the curved surface extending between an edge of the first planar surface and an edge of the second planar surface. In an embodiment, the curved surface may extend from the edge of the first planar surface to the edge of the second planar surface.

In an embodiment, an optical component may include generally planar first and second surfaces, and a concave surface. The first surface may be arranged at a predetermined angle relative to the second surface such that, when a light beam enters the optical component at the second surface, the light beam passes through the optical component and is reflected at the first surface. The predetermined angle may be an acute angle, e.g., 45 degrees. The second surface may be mirrored to facilitate reflection of light incident thereon through the optical component.

The concave surface may include generally opposing edges that are spaced apart along an axis extending orthogonally from the second surface and arranged such that light reflected by the first surface is directed towards the concave surface. The generally opposing edges may extend in a direction parallel to a direction that a longitudinal dimension of the concave surface extends, wherein the direction in which the opposing edges extend is orthogonal to the axis extending from the second surface. The concave surface is adapted such that a light beam reflected form the first surface is emitted at the concave surface such that a first portion of the emitted beam in a first plane is focused at a first distance from an imaginary plane extending through the generally opposing edges of the concave surface, and a second portion of the emitted beam in a second plane is focused at a second distance from the imaginary plane, the first distance being greater than the second distance.

An optical system may include a lens system through which a beam of light is transmitted and a first optical component operatively coupled to the lens system. The first optical component may include generally planar first and second surfaces, and a concave surface. The generally planar first and second surfaces may be arranged to reflect the beam of light passing through the optical component at the second surface. The second surface may be at a predetermined angle relative to the first surface. The concave surface may include generally opposing edges that are spaced apart along an orthogonal axis extending through the second surface.

The optical system may also include a second optical component disposed such that a light beam emitted at the concave surface passes through the second optical component. The first and second optical components may be adapted such that, when a light beam passes through the first and second optical components and is emitted from the second optical component, a first astigmatism is caused to the light beam by the first optical component and a second astigmatism is caused to the light beam by the second optical component, the combination of the first and second astigmatisms resulting in the light emitted from the second optical component having substantially no astigmatism.

In accordance with an aspect of the technology, a lens combination may include a first lens and a second lens. The first lens may have a generally planar first lens end surface defining an oval edge. The second lens may have a generally planar second lens end surface operatively coupled to the first lens end surface. The second lens may have four primary edges and at least two secondary edges connecting pairs of the primary edges. Each of the primary edges may extend in substantially a straight line between two spaced-apart points at the oval edge of the first lens.

In some arrangements, an entirety of the second lens end surface may be arranged facing the first lens end surface.

In some arrangements, at least one of the secondary edges of the second lens end may be curved.

In some arrangements, the first lens and the second lens may be configured such that a light beam exiting the first lens at the first lens end surface may enter the second lens at the second lens end surface. In some such arrangements, the second lens may further include a generally planar second lens angled surface and a second lens exit surface. The second lens end surface may be arranged at a predetermined angle relative to the second lens angled surface such that a light beam entering the second lens at the second lens end surface may be reflected at the second lens angled surface. The second lens exit surface may be arranged such that light reflected by the second lens angled surface may be directed towards the second lens exit surface.

In some arrangements, the second lens exit surface may be a concave surface curving inwardly towards an interior of the second lens.

In some arrangements, the concave surface of the second lens may include generally opposing first and second edges. In some such arrangements, the generally opposing first and second edges may extend along respective first and second axes in which the first axis may confront or be coextensive with the second lens end surface.

In some arrangements, the oval edge of the first lens end surface may be in the shape of a circle, the primary edges of the second lens may extend along respective primary edge axes, and the primary edge axes may intersect to define a square.

In accordance with another aspect of the technology, an optical probe may include a lens combination, an optical fiber assembly including an optical fiber, and a cover circumferentially surrounding the optical fiber assembly. The lens combination may include a first lens and a second lens. The first lens may have a generally planar first lens end surface defining an oval edge. The second lens may have a generally planar second lens end surface operatively coupled to the first lens end surface. The second lens may have four primary edges and at least two secondary edges connecting pairs of the primary edges. Each of the primary edges may extend in substantially a straight line between two spaced-apart points at the oval edge of the first lens. The optical fiber assembly and the lens combination may be configured such that a light beam exiting the optical fiber enters the lens combination at an entering surface of the first lens, passes through the first lens, and exits the first lens at the first lens end surface.

In accordance with another aspect of the technology, an optical probe may include a lens combination, an optical fiber assembly including an optical fiber, and a first cover circumferentially surrounding the optical fiber assembly. The lens combination may include a first lens and a second lens. The first lens may have a generally planar first lens end surface defining an oval edge. The second lens may have a generally planar second lens end surface operatively coupled to the first lens end surface. The second lens may have four primary edges and at least two secondary edges connecting pairs of the primary edges. Each of the primary edges may extend in substantially a straight line between two spaced-apart points at the oval edge of the first lens. The optical fiber assembly and the lens combination may be configured such that a light beam exiting the optical fiber enters the lens combination at an entering surface of the first lens, passes through the first lens, and exits the first lens at the first lens end surface. The first lens and the second lens may be configured such that a light beam exiting the first lens at the first lens end surface may enter the second lens at the second lens end surface. In some such arrangements, the second lens may further include a generally planar second lens angled surface and a second lens exit surface. The second lens end surface may be arranged at a predetermined angle relative to the second lens angled surface such that a light beam entering the second lens at the second lens end surface may be reflected at the second lens angled surface. The second lens exit surface may be arranged such that light reflected by the second lens angled surface may be directed towards the second lens exit surface.

In some arrangements, the first cover may substantially surround the lens combination.

In some arrangements, the optical probe may further include a second cover overlapping the first cover.

In some arrangements, the second cover may be a torque coil configured to exert torque on the optical probe such that the second lens is rotated about a longitudinal axis defined by the optical fiber.

In accordance with another aspect of the technology, an optical probe may include an optical fiber assembly including an optical fiber, an optical component assembly and a first cover circumferentially surrounding the optical fiber assembly. The optical component assembly may include a first optical component having a first end surface and a second optical component operatively coupled to the first optical component. The second optical component may have a second end surface confronting the first end surface of the first optical component. The second end surface of the second optical component may be attached to the first end surface of the first optical component by an adhesive that at least partially circumferentially surrounds the second end surface of the second optical component. The first cover may circumferentially surround the optical fiber assembly. The adhesive may attach the second optical component to the first cover.

In some arrangements, the adhesive may be bounded by the first cover.

In some arrangements, the first optical component and the second optical component may be configured such that a light beam exiting the first optical component lens at the first end surface enters the second optical component at the second end surface. The second optical component may further include a generally planar angled surface and an exit surface. The second end surface may be arranged at a predetermined angle relative to the angled surface such that a light beam that enters the second optical component at the second end surface is reflected at the angled surface. The exit surface may be arranged such that light reflected by the angled surface is directed towards the exit surface.

In some arrangements, the exit surface of the second optical component may be a concave surface curving inwardly towards an interior of the second optical component.

In some arrangements, the first optical component may be a graded-index (GRIN) lens. In some such arrangements, the optical probe may further include a glass spacer rod positioned within the first cover between the GRIN lens and the optical fiber.

In some arrangements, the optical probe may further include a second cover overlapping the first cover.

In some arrangements, the second cover may be a torque coil configured to exert torque on the optical probe such that the second optical component is rotated about a longitudinal axis defined by the optical fiber.

In accordance with another aspect of the technology, an optical probe may include an optical fiber assembly, an optical component assembly, a first cover, a first material, and a second material. The optical fiber assembly may include an optical fiber. The optical component assembly may include a first optical component and a second optical component. The first optical component may have a first end surface. The second optical component may have a second end surface that may confront the first end surface of the first optical component. The second end surface of the second optical component may be attached to the first end surface of the first optical component by the first material that may at least partially circumferentially surround the second end surface of the second optical component. The first material may circumferentially surround an edge of the second optical component surrounding the second end surface of the second optical component and thereby remove any space between the first cover and the edge of the second optical component in a radial direction from the edge of the second optical component to the first cover. The first cover may be attached to and may circumferentially surround the optical fiber assembly. The second adhesive may attach the second optical component to the first cover.

In some arrangements, the first adhesive may be the same as the second adhesive. In some arrangements, the first adhesive may be different from the second adhesive.

In some arrangements, the first adhesive may be bounded by the first cover.

In some arrangements, the first optical component and the second optical component may be configured such that a light beam exiting the first optical component lens at the first end surface may enter the second optical component at the second end surface. In some such arrangements, the second optical component may further include a generally planar angled surface and an exit surface. The second end surface may be arranged at a predetermined angle relative to the angled surface such that a light beam that enters the second optical component at the second end surface is reflected at the angled surface. The exit surface may be arranged such that light reflected by the angled surface is directed towards the exit surface.

In some arrangements, the exit surface of the second optical component may be a concave surface curving inwardly towards an interior of the second optical component.

In some arrangements, the first optical component may be a GRIN lens. In some such arrangements, the optical probe may further include a glass spacer rod positioned within the first cover between the GRIN lens and the optical fiber.

In some arrangements, the optical probe may further include a sheath. In some such arrangements, the optical fiber may define a longitudinal axis. The first cover may define an opening that may be radially offset from the longitudinal axis and that may overlie the second optical component. In some arrangements, the sheath may cover the opening. In some such arrangements, at least a portion of the sheath covering the opening may be flat. In some such arrangements, the portion of the sheath covering the opening or the entirety of the sheath may have a thickness in the range of 5-50 μm. In some arrangements, the opening may overlie the exit surface of the second optical component. In some arrangements, the sheath may cover the distal end of the optical probe.

In some arrangements, the optical probe may further include a second cover overlapping the first cover. In other arrangements, the optical probe may further include a second cover underlapping the first cover.

In some arrangements, the second cover may be a torque coil. In such arrangements, the torque coil may be configured to exert torque on the optical probe such that the second optical component may be rotated about a longitudinal axis defined by the optical fiber.

In some arrangements, the optical fiber may define a longitudinal axis. In such arrangements, the second cover may be configured to cover a terminal end of the optical probe to prevent exposure of the second optical component at the terminal end. In such arrangements, the longitudinal axis of the optical fiber may pass through the second cover.

In some arrangements, the first cover may include an inner sleeve and an outer sleeve that may be attached to and may circumferentially surround the inner sleeve. In some such arrangements, the first cover may further include a torque coil attached to the outer sleeve. In such arrangements, the torque coil may be configured to exert torque on the optical probe.

In some arrangements, the optical fiber may define a longitudinal axis. In such arrangements, the optical probe may further include a terminal end that may define an opening that exposes the second optical component. In such arrangements, the longitudinal axis of the optical fiber may pass through the opening.

In some arrangements, the optical fiber may be attached to the first optical component such that the first cover may be spaced apart from an exposed surface of the optical fiber to form a gap between the first cover and the exposed surface of the optical fiber. In such arrangements, the gap may be defined by at least the exposed surface of the optical fiber, the first cover, and the first optical component. In some arrangements, the gap may be filled with air.

In some arrangements, the first cover may include an inner sleeve and an outer sleeve. The inner sleeve may be attached to the outer sleeve by a third adhesive. The outer sleeve may circumferentially surround the inner sleeve. The inner sleeve may be attached by the third adhesive to the first optical component. In such arrangements, the gap defined by at least the exposed surface of the optical fiber, the first cover, and the first optical component may be filled with the third adhesive or another adhesive.

In some arrangements in which the first cover includes the inner sleeve and the outer sleeve, the first adhesive and the third adhesive may be the same adhesive. In some such arrangements, the second adhesive may be different from the first adhesive and the third adhesive.

In some arrangements, the optical probe may further include a glass spacer rod that may be attached to the first optical component. In some such arrangements, the optical fiber may further include a core, a cladding surrounding the core, and a jacket surrounding only a first portion section of the cladding. In such arrangements, the spacer rod may be attached to the core and a second portion of the cladding different from the first portion.

BRIEF DESCRIPTION OF THE DRAWINGS

By way of description only, embodiments of the present disclosure are described herein with reference to the accompanying figures, in which.

DETAILED DESCRIPTION

An x-y-z coordinate system having mutually orthogonal x, y, and z axes is used in FIGS. 1A-3B and referred to in the description below to describe the configuration of optical components of the present disclosure, where the x, y, z axes form planes x-y, x-z, and y-z. In addition, reference is made to x, y, and z axial lines to describe structural features of an optical component extending in a direction parallel to or along the x, y, and z axes, respectively.

Figure 1A:
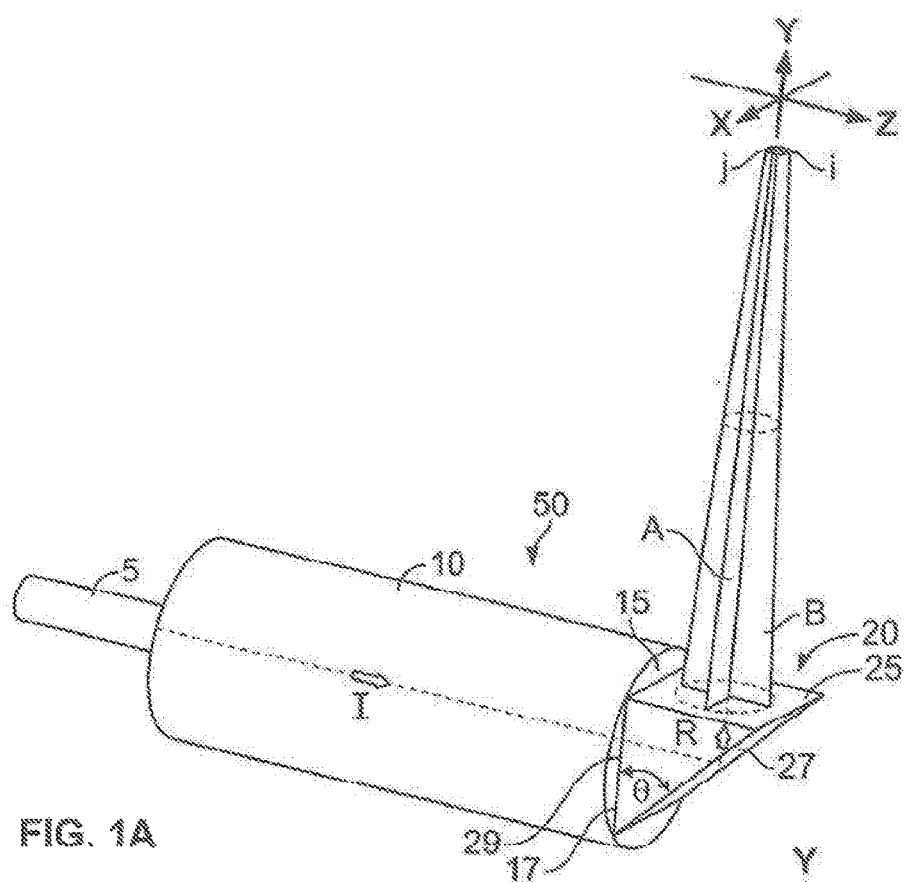
FIG. 1A is a perspective view of an optical assembly.
Figure 1B:
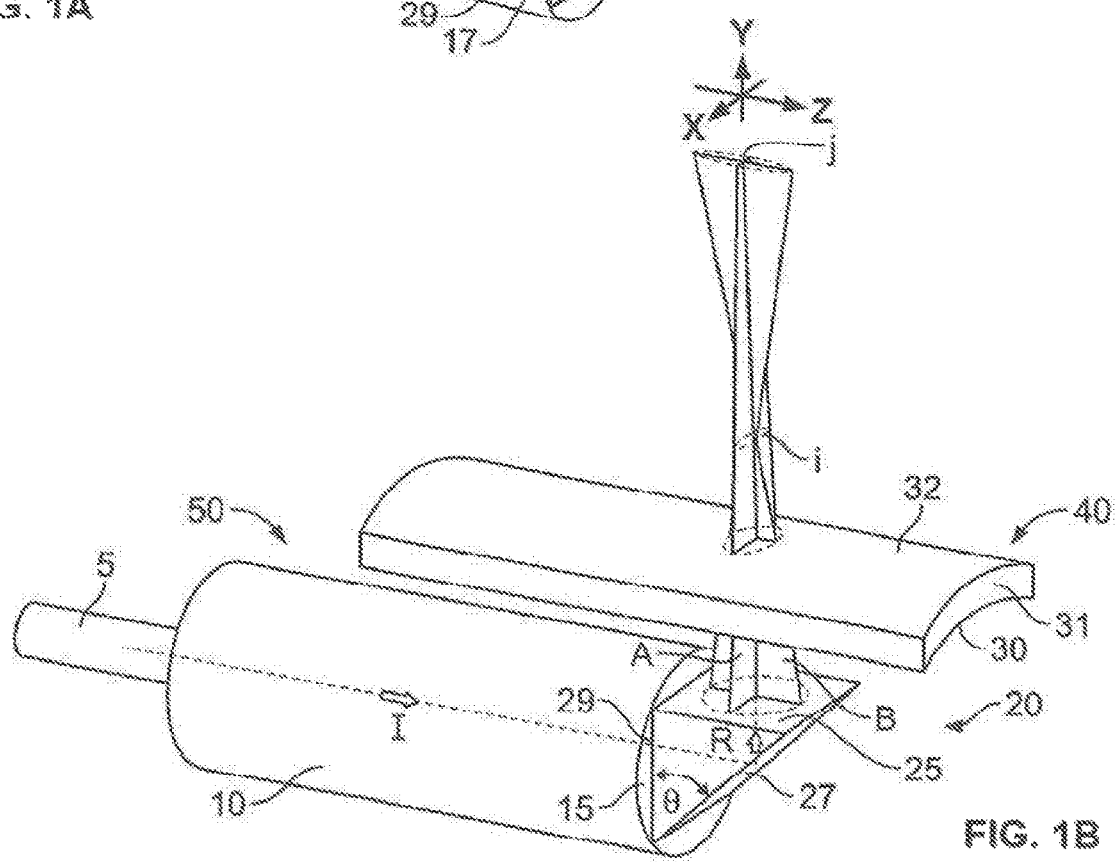
FIG. 1B is a perspective view of the optical assembly of FIG. 1A shown relative to another optical component.

An optical assembly 50 is described with reference to FIGS. 1A and 1B. The optical assembly 50 includes an optical fiber 5, an optical lens system 10 and an optical component or prism 20. The lens system 10 may include one or more optical lenses (not shown) that transmit light supplied from the optical fiber 5 to the optical component 20. The optical component 20 is coupled to the lens system 10 at an optical interface 15. The optical interface 15 is formed by a planar surface 17 of the lens system 10 that faces and is in contact with a planar surface 29 of the optical component 20. The optical component 20 is made of a transparent material, such as plastic or glass, and is configured in the form of a prism having surfaces arranged to reflect and then emit light supplied from the lens system 10 in a predetermined direction.

Referring again to FIGS. 1A-1B, the optical component 20 is in the shape of a triangular prism including the planar surface 29, a planar surface 27, and a planar surface 25. The surface 29 extends in a plane parallel to the x-y plane. The surface 25 extends in a plane parallel to the x-z plane. The surface 27 and the surface 29 define an angle θ, e.g., 45 degrees, therebetween.

The effect the optical component 20 has on light that is passed through the optical component 20 and then emitted from the optical component 20 at the surface 25 is now described. For simplicity, it is assumed that a light beam I supplied from the fiber 5 to the lens system 10 is transmitted by the lens system 10 so that the light beam I is traveling in the z axis direction when incident on the surface 29 of the optical component 20, and that the light beam I incident upon the surface 29 of the optical component 20 does not have astigmatism. The light beam I incident on the surface 29 travels through the optical component 20 in the direction of the z-axis to the planar surface 27. Based on the angle of incidence of the light beam I at the surface 27, which is at an angle θ relative to surface 29, the surface 27 reflects the beam I in the direction R, where the direction R is generally in the y-axis direction, toward the surface 25. The reflected light beam I is then emitted from the optical component 20 at the surface 25. It is further assumed that the reflected light beam I that is emitted at the surface 25 does not have astigmatism.

The light beam I that is emitted from the optical component 20 at the surface 25 is formed from rays traveling in the orthogonal x-y and y-z planes, as represented by the planar shapes A, B, respectively. As shown in FIG. 1A, since the surface 25 is planar, i.e., not curved, the beam waists j, i, i.e., the location at which the spot size of the beam is at a minimum, in the x-y plane (planar shape A) and y-z plane (planar shape B), respectively, are at the same position.

Positioning a transparent element 40, e.g., a lens, in the path of the light emitted from the optical component 20 at the surface 25 may have an effect upon the emitted light, where the effect depends on the shape and optical properties of the element 40. As shown in FIG. 1B, a transparent element 40, such as a concave lens having concave shaped surfaces 30 and 32, may be positioned over the surface 25 of the optical component 20 such that the reflected light emitted at the surface 25 passes through the surface 30, portion 31 of the lens 40 between the surfaces 30 and 32, and then is emitted from the element 40 at the surface 32. As shown in FIG. 1B, after the light emitted at the surface 25 passes through the concave lens 40, the beam waist i in the y-z plane (shape B) is closer to the surface 25 than the beam waist j in the x-y plane (shape A).

The effect that a lens, which has curved surfaces, such as concave lens 40, and is external to a first optical component of an optical device, and through which light emitted from the first optical component passes, has upon the light emitted from the first optical component, may be compensated for by having the light pass through another, second optical component with a curved surface, i.e., another lens, of the optical device before the light is emitted from the first optical component of the optical device toward the external lens. As discussed above (see FIG. 1B), the curved shape of the surfaces 30 and 32 of the lens 40 may cause the light emitted from the optical component 20 to have astigmatism.

By providing another, second optical component in the form of a lens with curved surfaces through which light passes before being emitted from a first optical component of an optical device toward an external lens, astigmatism may be caused in the light emitted from the first optical component to compensate for the astigmatism caused by the external lens, such that the light ultimately emitted from an optical system including the optical device and the external lens has minimal or no astigmatism.

Figure 2A:
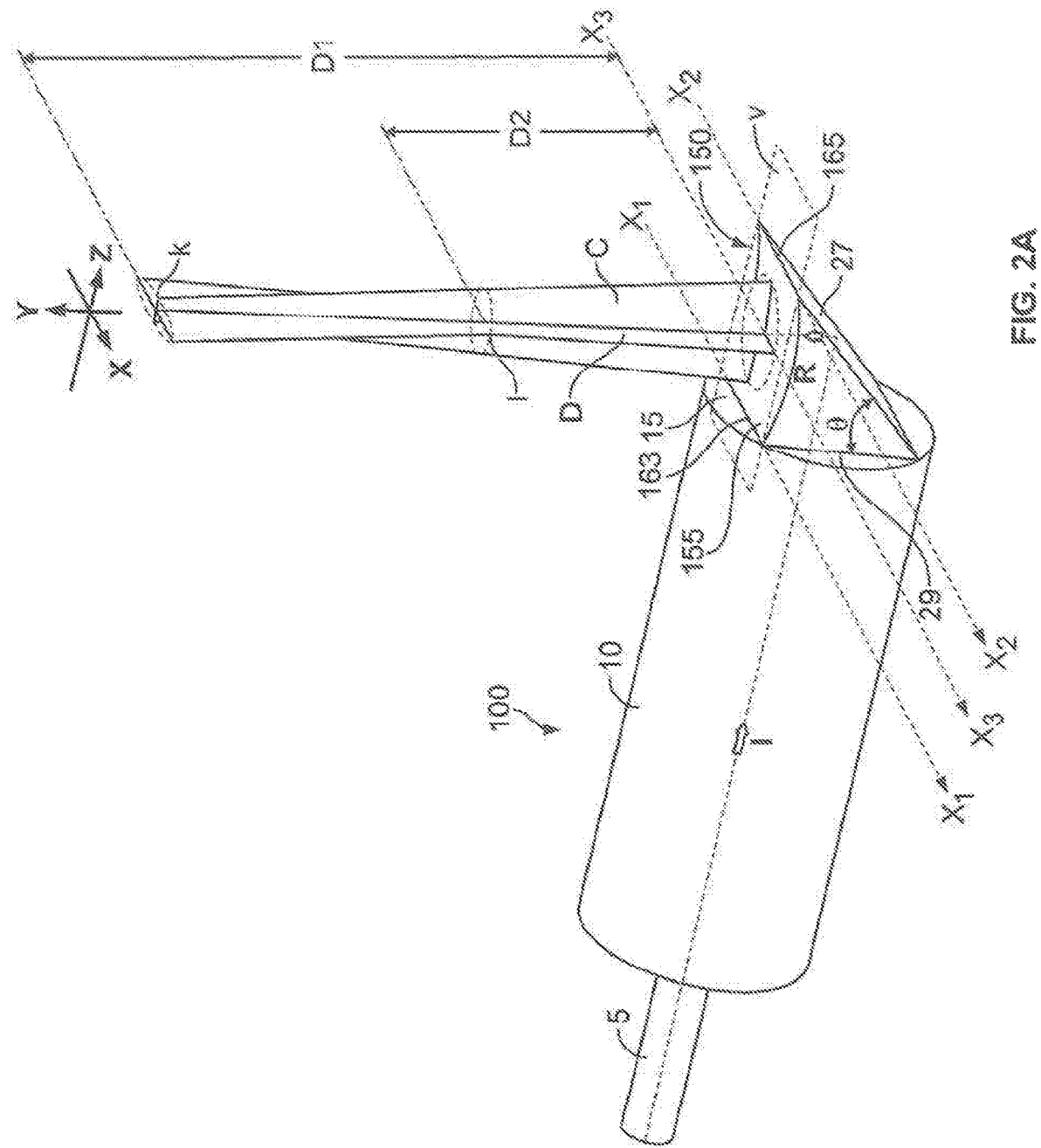
FIG. 2A is a perspective view of another optical assembly with an optical component thereof omitted.
Figure 2B:
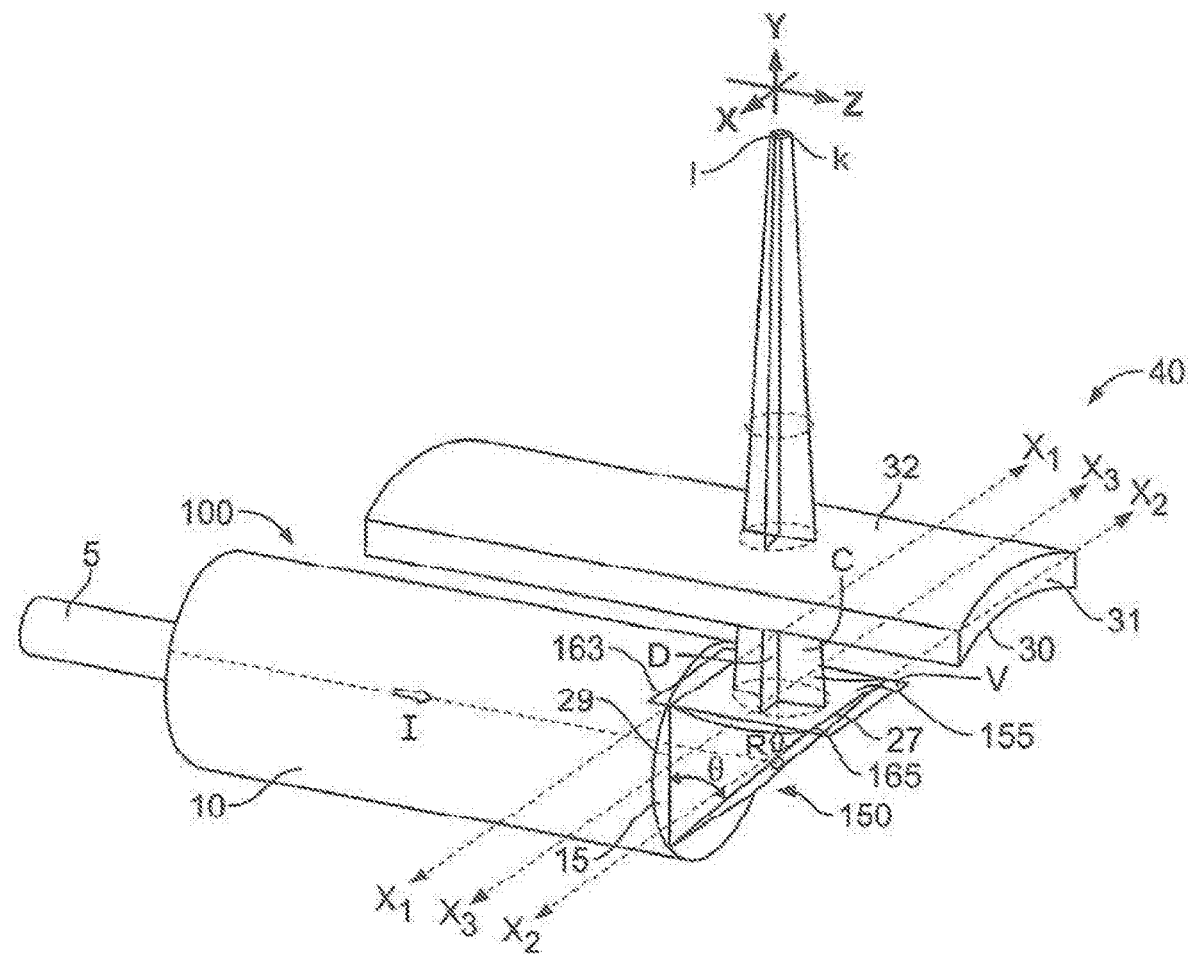
FIG. 2B is a perspective view of the optical assembly of FIG. 2A shown including the optical component omitted from FIG. 2A.

In an embodiment as shown in FIGS. 2A-2B, an optical assembly 100 includes an optical component 150 having a concave surface 155. The optical assembly 100 is substantially similar to the optical assembly 50 with the exception that optical component 20 has been replaced by optical component 150. The optical assembly 100 includes optical fiber 5 and optical lens system 10, as in the optical assembly 50, and the optical component 150. The optical component 150 is similar to the optical component 20 with the exception that the optical component 150 includes the concave surface 155 as opposed to planar surface 25. The optical component 150 is coupled to the lens system 10 at optical interface 15, which is formed by planar surface 17 that contacts planar surface 29 of the optical component 150.

The concave surface 155 is a plane curve defined between a first edge 163, which extends in a direction of an axial line x1, and a second edge 165, which extends in a direction of an axial line x2. The plane curve of the surface 155 extends in a negative y-axis direction from each of the first and second edges 163, 165, forming a concave surface that bulges inwardly in a direction away from an imaginary x-z plane V, which extends through the edges 163, 165 of the component 150. The concave surface 155 has a longitudinal dimension extending in a direction of the x-axis and an axial line x3 extends through points of greatest depth along the longitudinal length of the concave surface 155. In some embodiments of the optical component 150, the edge 163 of the concave surface 155 is also the edge of the planar surface 29 such that the concave surface 155 and the planar surface 29 share a common edge extending in a straight line, and the edge 165 of the concave surface 155 is also the edge of the planar surface 27 such that the concave surface 155 and the planar surface 27 share a common edge extending in a straight line. Similar to the optical assembly 50, when a light beam I is incident upon the surface 27 of the optical component 25 of the assembly 100, the light beam enters and passes through the component 150 and is reflected by surface 27 in direction R generally in the y-axis direction and toward concave surface 155.

As shown in FIG. 2A, the concave surface 155 is adapted such that the light emitted from the optical component 150 at the surface 155 has the characteristics that the portion of the emitted light that is in the y-z plane (represented by planar shape C) has a beam waist k that is at a first distance D1 from imaginary x-z plane V, and the portion of the emitted light that is in the x-y plane (represented by planar shape D) has a beam waist l that is at a second distance D2 from the plane V, where the first distance D1 is greater than the second distance D2. In particular, the portion of the emitted light in the x-y plane (represented by planar shape D) propagates away from the surface 155 as a converging beam portion that converges to the beam waist l at the second distance D2, and then propagates as a diverging beam portion from the second distance D2 to distances greater than the second distance D2 from the plane V. In other words, the portion of the emitted light that is in the x-y plane (represented by planar shape D) propagates as a diverging, i.e., widening, beam portion as the distance the beam portion propagates away from a distance D2 from the surface 155 increases. The portion of the emitted light in the y-z plane (represented by planar shape C) propagates away from the surface 155 as a converging beam portion that converges to a beam waist k after propagating a first distance D1 from the plane V, which is a greater distance away from the surface 155 than the distance that the portion of the emitted light in the x-y plane (represented by planar shape D) propagates before converging to the beam waist l. The first distance D1 from the plane V at which the beam waist k of the portion in the y-z plane is located is a function of the concavity of the surface 155, such that the greater the concavity of the surface 155 in the negative y-axis direction, the greater the first distance D1. Conversely, the lesser the concavity of the surface 155 in the negative y-axis direction, the smaller the first distance D1.

The degree of concavity of the surface 155 may be selected in view of the curvature of surfaces of an external optical component, such as the surfaces 30, 32 of the component 40, through which the light emitted at the surface 155 is to pass through, such that the light emitted from the optical component 150 and then passes through the external component 40 is emitted from the component 40 with minimal or no astigmatism.

As shown in FIG. 2B, the component 150 may be provided with the curved surface 155 such that the beam waists k, l in the y-z plane (planar shape C) and in the x-y plane (planar shape D) respectively of the light beam I emitted from the lens 40 are at the same distance from the imaginary plane V.

During use, the optical assembly 100 may be used to illuminate objects or structures. Medical uses for the optical assembly 100 may include illuminating internal body structures during a minimally invasive surgical procedure. The optical assembly 100 may be adapted such that the spot size of the light beam emitted from the assembly 100 may correspond with the structures that are desired to be illuminated. In an embodiment, the light beam emitted from the assembly 100 may be elliptical and have a spot size of approximately between 5 and 100 µm. In an embodiment, the assembly 100 may be adapted to provide that the spot size of the emitted light beam may facilitates the illumination and identification of particular cells, e.g., cancer cells.

Figure 3A:
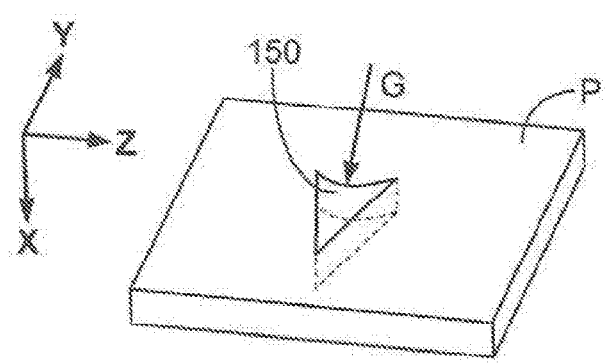
FIG. 3A is a perspective view of a plate from which a prism has been cut, in accordance with an embodiment of the present disclosure.
Figure 3B:
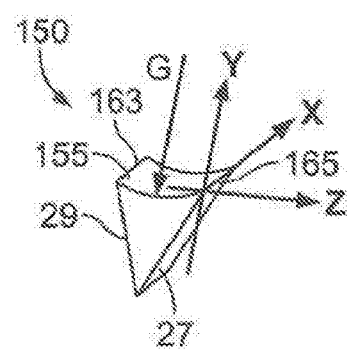
FIG. 3B is a perspective view of the prism cut from the plate of FIG. 3A.

A method of manufacturing the optical component 150 is described with reference to FIGS. 3A and 3B. As shown in FIG. 3A, a plate P, e.g., a glass or a polymer, is provided. Optical component 150 may be cut from the plate P. The shape of the optical component 150 is formed by cutting the desired shape from the plate P. The planar surfaces 27 and 29 may be formed by using a tool, such as a laser or other cutting instrument, that cuts depth-wise, in a direction of the x axis, into the plate P. Further, the concave surface 155 may be formed by using the same tool and cutting depth-wise into the plate P, in a direction of the x axis, along a desired radius of curvature G. The shape of the optical component 150, thus, may be completely formed by cutting only depth-wise, in a direction of the x axis, into the plate P. The manufacture of the optical component 150 is easily performed simply by cutting depth-wise into the plate, and there is no need to perform any further cutting or shaping after removal of the optical component 150 from the plate P, following such cutting.

Figure 4A:
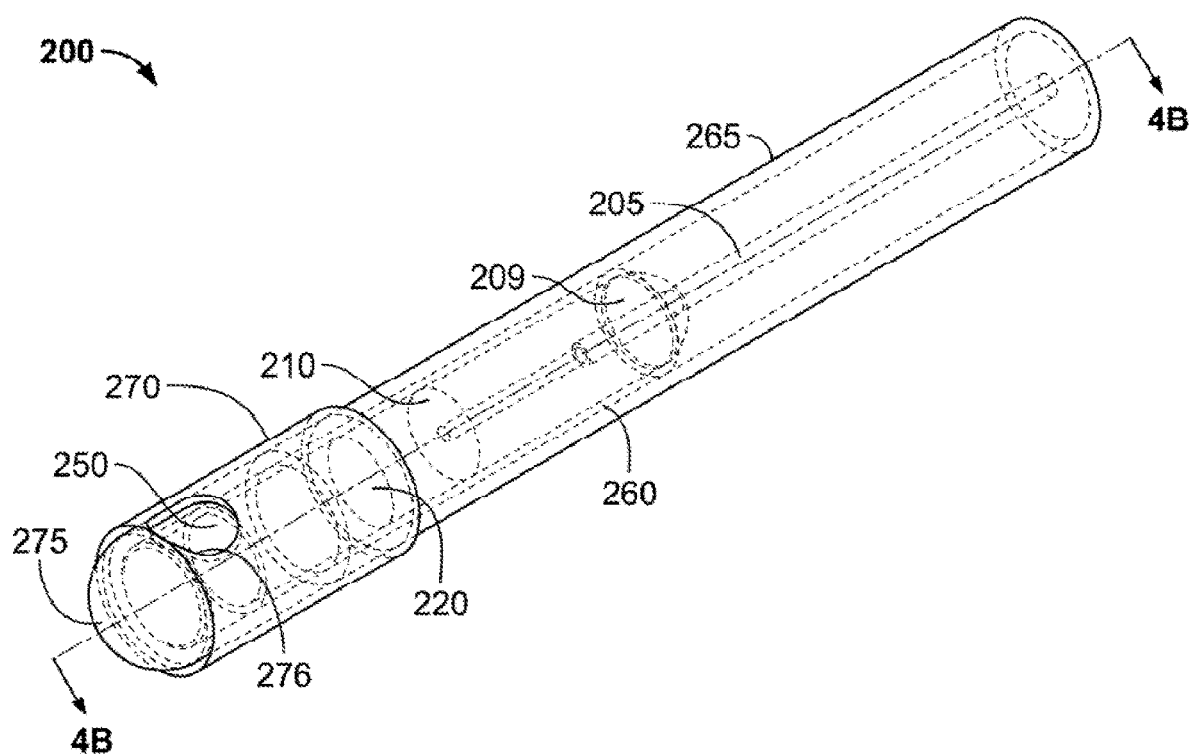
FIG. 4A is a perspective view of an optical probe in accordance with an embodiment.
Figure 4B:
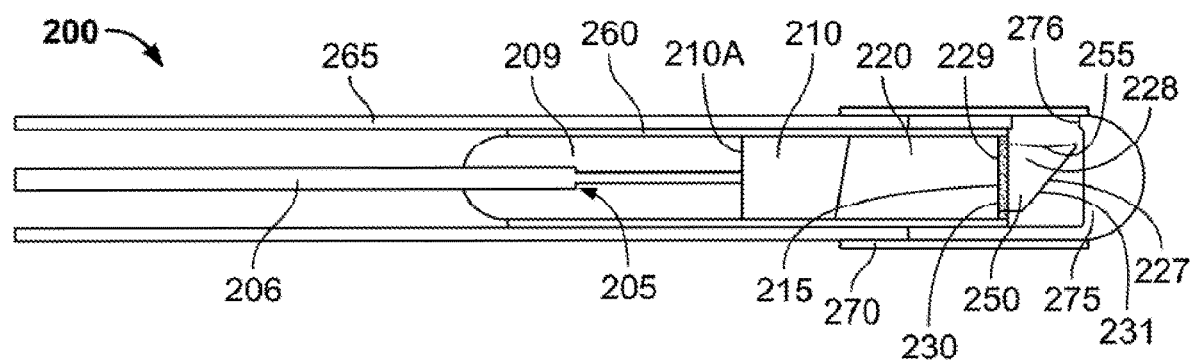
FIG. 4B is a cross-sectional view of the optical probe of FIG. 4A along the lines 4B-4B.

Referring now to FIGS. 4A and 4B, optical probe 200 generally includes optical fiber 205, potting 209, spacer 210, first optical component 220 which as in this example may be a GRIN lens, second optical component 250 which as in this example may be but is not limited to being a prism lens, inner cover 260 which as in this example may be in the form of a sheath or tube, exterior cover 265 which as in this example may be in the form of a sheath or tube, and outer cover 270 which as in this example may be in the form of a sheath or tube, and end cap 275.

Optical fiber 205 may be but is not limited to being a conventional optical fiber. Optical fiber 205 may be formed by a core, cladding surrounding the core and jacket 206 surrounding the cladding. Jacket 206 may be a coating, such as but not limited to an acrylic, urethane, or epoxy, which in some arrangements may be applied and cured onto the cladding of the optical fiber at the time the fiber is fabricated. A portion of jacket 206 may be stripped away to expose the cladding. A portion of jacketed optical fiber 205 including the exposed cladding portion of the optical fiber 205 may extend through and be circumferentially surrounded by potting 209 and into abutment against surface 210A of spacer 210 that is substantially perpendicular to a longitudinal axis defined by optical fiber 205. Potting 209 may be made of an adhesive, such as but not limited to epoxy, such that upon curing the outer surface of the portion of optical fiber 205 within potting 209 may conform to and be held rigidly by the potting. In this manner, potting 209 may be self-adhered to spacer 210 such that an end surface of optical fiber 205 is held in abutment with surface 210A of the spacer. Additionally, optical fiber 205 preferably may be fused to surface 210A of spacer 210, such as by heating the fiber, before potting 209 is applied about the fiber. In such arrangements, a portion of jacket 206 may be stripped away to expose the cladding of optical fiber 205 and after fusing the fiber to surface 210A of spacer 210, coating 207 (see, e.g., FIG. 8B) which may be but is not limited to being an epoxy, urethane, acrylic, or polyimide coating may be applied to the cladding of the optical fiber. In some such arrangements, a greater amount of coating 207 may be applied near the interface of optical fiber 205 and spacer 210 such that the coating is thicker in that region than elsewhere along the coated cladding of the optical fiber (as shown in FIG. 8B, for example). In this manner, the distal end of optical fiber 205 may be better supported to prevent separation of the optical fiber from spacer 210 during higher rotational speeds of the optical probe.

As in the example shown, spacer 210 may be substantially in the form of a cylindrical rod and may be transparent such that a light beam emitted by optical fiber 205 enters the spacer at surface 210A and passes through the spacer. In some arrangements, spacer 210 may be but is not limited to being made of glass. Spacer 210 and first optical component 220 may have complementary end surfaces, i.e., facets, set at oblique angles to each of their longitudinal axes which may reduce beam reflection back into optical fiber 205 from a light beam emitted from the optical fiber. In this manner, as shown, the complementary end surfaces of spacer 210 and first optical component 220 may be in abutment with each other. First optical component 220 and spacer 210 may be attached to each other such as but not limited to by an adhesive, such as but not limited to epoxy, applied along their complementary end surfaces or by being heated to fuse their complementary end surfaces together.

Second optical component 250 may be substantially the same as optical component 150 described previously herein, and thus features of second optical component 250 with like reference numerals as those of the features of optical component 150 have essentially the same form and serve essentially the same purpose as the corresponding features of optical component 150. In this manner, a light beam emitted from optical fiber 205 may pass through spacer 210, pass through first optical component 220, enter second optical component 250 through planar first surface 229, be reflected at planar angled surface 227, and be emitted from exit surface 255, which may be a concave surface as in the example shown or alternatively a planar surface, of the second optical component. A first end of second optical component 250 which includes and defines first surface 229 may be affixed by adhesive 230, such as by but not limited to being by epoxy, to optical interface surface, i.e., facet, 215 at an end of first optical component 220 opposite the end of the first optical component having the surface complementary to the obliquely angled end surface of spacer 210. In some arrangements, planar angled surface 227 may be coated with a reflective coating 231 to avoid attachment of potential contaminants on the angled surface such that an interface of the angled surface and the reflective coating provides complete or substantially complete internal reflection of light which impinges the angled surface from within second optical component 250. The potential contaminants may even include an adhesive coating over the reflective coating that may be used to add mechanical strength. Coating 231 may be a polymer resin, which may be but is not limited to being a dielectric thin film applied using a known thin film deposition process, or metallization applied by an evaporation technique known to those skilled in the art. Such a dielectric coating may be but is not limited to being made of a polymer or combination of polymers, or more preferably may be stacked layers, e.g., alternating layers, of silicon dioxide ($SiO_2$) and titanium dioxide ($TiO_2$) or other metal oxide that may be deposited, for example, by way of an evaporation process for forming evaporated coatings or a physical vapor deposition (PVD) process such as sputtering. In a preferred arrangement, the dielectric coating may include four (4) alternating layers of $SiO_2$ and $TiO_2$. Appropriate reflective metals for the metallization may be but are not limited to being aluminum, silver, and gold. In some other arrangements, planar angled surface 227 may be uncoated when the angled surface is directly exposed to air, and in such arrangements the interface of the angled surface with air may provide for complete or substantially complete internal reflection of light which impinges the angled surface from within second optical component 250. Coating 231, thus, may be provided such that internal reflection at planar angled surface 227 is the same or substantially the same as when the coating is absent and the angled surface is directly exposed to air.

As further shown in FIGS. 4A and 4B, inner cover 260 may extend along a length of and circumferentially surround potting 209, spacer 210, and first optical component 220 as well as a portion of second optical component 250. As in the example shown, inner cover 260 may be a thin tube which, in some arrangements, may be formed of a polymer resin such as but not limited to polyethylene terephthalate (PET) which may be heat shrunk to various components and an adhesive such as epoxy. PET tubing, when used, may be coated with an adhesive at any portions of the tubing interfacing with other components. In this manner, inner cover 260 may be adhered to all or at least portions of outer surfaces of each of potting 209, spacer 210, and first optical component 220 such that the inner cover may conform to these components. As a result, potting 209, spacer 210, and first optical component 220 may be fixed together and held in axial alignment along a common longitudinal axis.

Exterior cover 265 may be affixed or otherwise adhered to inner cover 260, such as by but not limited to being by an adhesive which may be but not limited to being a high strength glue, e.g., heat curable epoxy, a urethane-based adhesive, or an acrylic adhesive. Exterior cover 265 may be but is not limited to being a torque coil for receiving and exerting torque to the entire assembly of optical probe 200. In this manner, exterior cover 265, and as a result optical probe 200, may be rotated by an attached motor at high speed up to at least 10,000 rpm. To withstand these rotational speeds, exterior cover 265 may have multiple layers of wound coils, and preferably two (2) or more layers of such coils which may be coiled in alternating directions. Exterior cover 265 may be but is not limited to being made of metals such as stainless steel.

As shown, exterior cover 265 may extend along only a portion of inner cover 260. In this manner, the remainder of inner cover 260 may be affixed to end cap 275, as shown. Exterior cover 265 may also be affixed to end cap 275 by an adhesive, such as but not limited to an epoxy. End cap 275 may be molded by a polymer resin, e.g., a high viscosity resin such as but not limited to heat curable epoxy, a urethane-based adhesive, or an acrylic adhesive. End cap 275 may extend distally from its attachment with inner cover 260 to beyond second optical component 250 such that the end cap surrounds second optical component 250 with the exception of cap opening 276. Cap opening 276 may have a sufficiently large diameter such that a light beam reflected from planar angled surface 227 and exiting exit surface 255 of second optical component 250 may pass through end cap 275 without obstruction. Cap opening 276 also may have a sufficiently small diameter such that the end cap may obstruct second optical component 250 from exiting the cap opening should the second optical component become dislodged from its attachment to first optical component 220.

As shown, adhesive 230 may extend around portion of a circumference of planar first surface 229 of second optical component 250, covering a portion of one or more side surfaces 228, planar angled surface 227, and exit surface 255 which extend from the second optical component. As shown in FIG. 4B, adhesive 230 may extend to an inner surface of inner cover 260 such that adhesive 230 is bound by second optical component 250 and the inner cover. In this manner, inner cover 260 may provide additional support to maintain the position of second optical component 250 against first optical component 220, especially in response to shear forces that may be imparted onto the second optical component during high speed rotation of optical probe 200.

In some arrangements, as shown, outer cover 270 may extend along only a portion of exterior cover 265 and along only a portion of end cap 275 at its maximum diameter. As further shown, outer cover 270 may overlie cap opening 276. In this manner, outer cover 270 may provide an additional barrier to prevent second optical component 250 from exiting cap opening 276 should the second optical component become dislodged from its attachment to first optical component 220. Outer cover 270 may be sufficiently thin such that the cover does not act as a lens to undesirably focus or disperse the light exiting exit surface 255 of second optical component 250 that passes through the cover, i.e., such that the cover causes little to no "lens effect" as known to those skilled in the art.

Figure 4C:
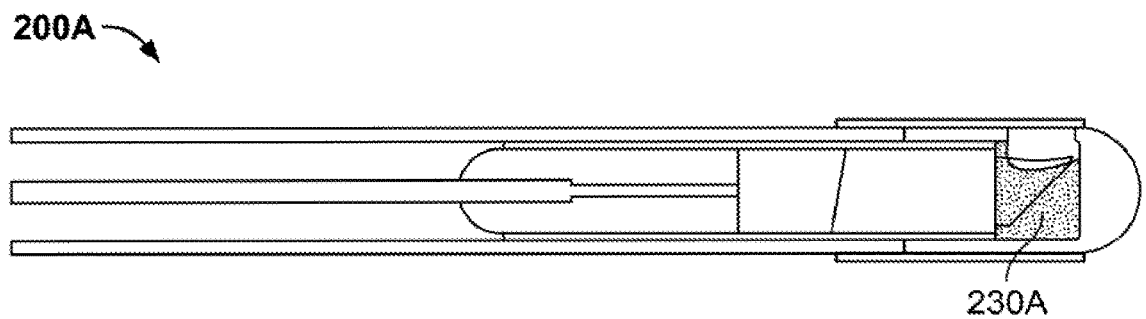
FIG. 4C is a cross-sectional view of an optical probe in accordance with another embodiment.

As shown in FIG. 4C, in an alternative arrangement, optical probe 200A may be the same or substantially the same as optical probe 200 with the exception that optical probe 200A may include adhesive 230A in place of adhesive 230. Unlike adhesive 230, adhesive 230A may substantially cover second optical component 250 and be further bound by resin cap 275. In such arrangements in which adhesive 230A surrounds angled surface 227 of second optical component 250, the second optical component may include reflective coating 231 covering the angled surface to provide complete or substantially complete internal reflection of light at the angled surface of the second optical component.

Figure 5A:
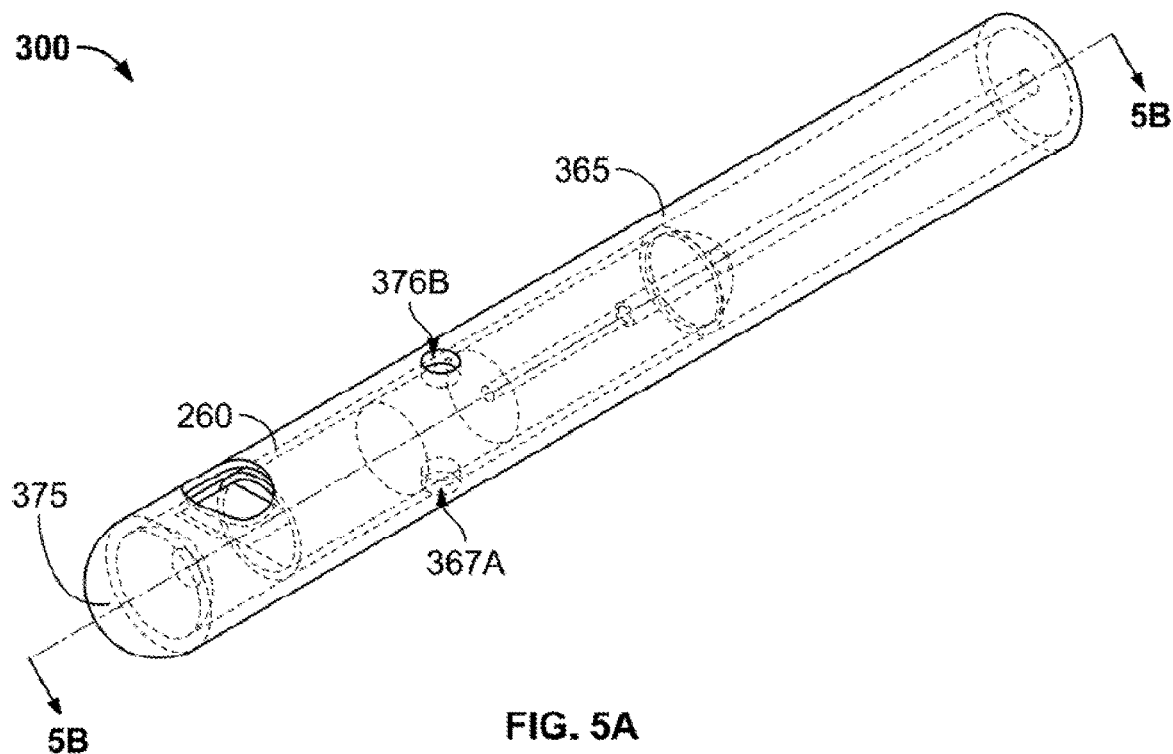
FIG. 5A is a perspective view of an optical probe in accordance with another embodiment.
Figure 5B:
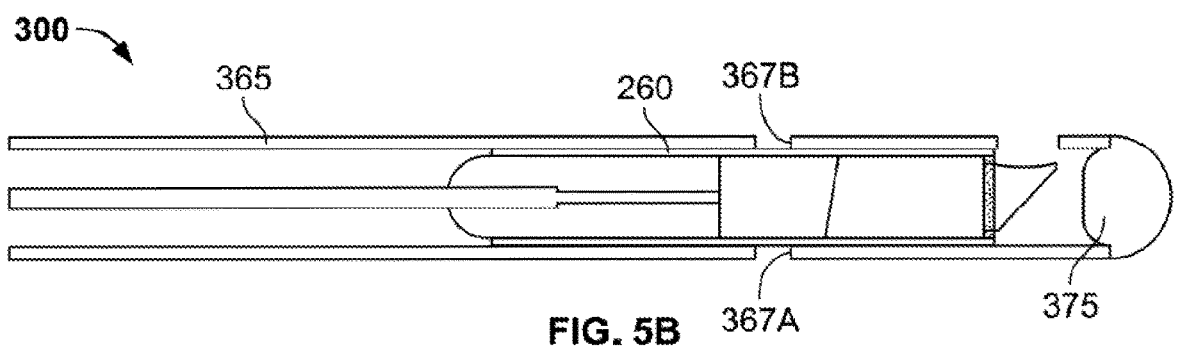
FIG. 5B is a cross-sectional view of the optical probe of FIG. 5A along the lines 5B-5B.

Referring now to FIGS. 5A and 5B, optical probe 300 may be substantially the same as optical probe 200 with the exception that optical probe 300 may include exterior cover 365 and end cap 375 in place of exterior cover 265 and end cap 275, respectively. Exterior cover 365 may be substantially the same as exterior cover 265 with the exception that exterior cover 365 may include a plurality of holes 367A, 367B to insert an adhesive such as but not limited to an epoxy, urethane, or acrylic adhesive. End cap 375 may be substantially the same as end cap 275 with the exception that end cap 375 may not contact inner cover 260. Instead, end cap 275 may be press-molded or glued into exterior cover 365 such that the end cap may be maintained in position during translation and high speed rotation of optical probe 300.

Figure 6:
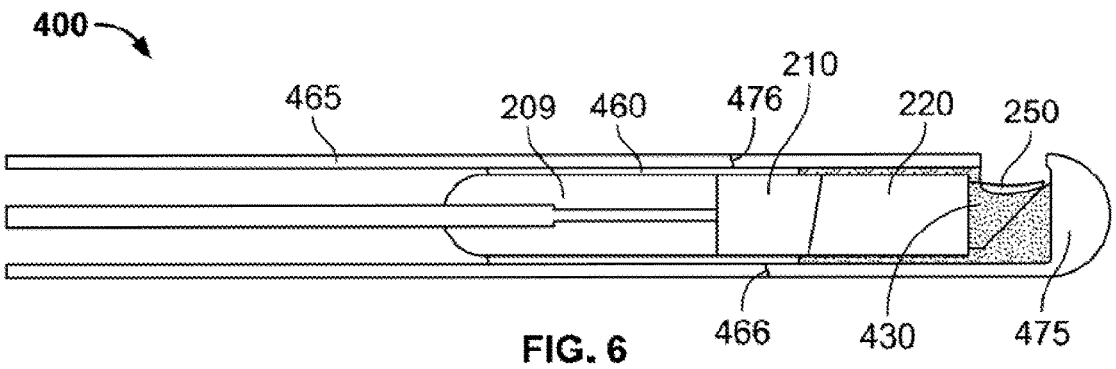
FIG. 6 is a cross-sectional view of an optical probe in accordance with another embodiment.

As shown in FIG. 6, optical probe 400 may be substantially the same as optical probe 200 with the exception that optical probe 400 may include inner cover 460, exterior cover 465, end cap 475, and adhesive 430 in place of inner cover 260, exterior cover 265, end cap 275, and adhesive 230, respectively. Inner cover 460 may be substantially the same as inner cover 260 with the exception that inner cover 460 may extend only along portions of potting 209 and spacer 210. Exterior cover 465 may be substantially the same as exterior cover 265 with the exception that exterior cover 465 may have an end face 466 that circumferentially surrounds spacer 210 and that is set at an oblique angle to the longitudinal axis of optical fiber 205. End cap 475 may be substantially the same as end cap 275 with the exception that end cap 475 may extend proximally to circumferentially surround spacer 210 and may have an end face 476 that is complementary to end face 466 of exterior cover 465. Alternatively, the exterior cover may extend further in a distal direction to first optical component 220 and the end cap may have a corresponding smaller length. In either alternative, adhesive 430 may be applied, as shown, to extend proximally such that the adhesive meets and attaches to inner cover 460. In this manner, adhesive 430 may provide even greater support of second optical component 250 during translation and high speed rotation of optical probe 400. In some alternative arrangements, the inner cover may extend to first optical component 220 and adhesive 430 may extend proximally a correspondingly shorter distance to meet and attach to the inner cover while still providing additional support to second optical component 250.

Additionally, as shown, adhesive 430 may fill a substantial portion of a space defined between end cap 475 and first optical component 220, providing still greater support of second optical component 250. In some embodiments where adhesive 430 surrounds angled surface 227 of second optical component 250, the second optical component may include reflective coating 231 covering the angled surface to provide for complete or substantially complete internal reflection of light at the angled surface of the second optical component. Further, due to the complementary angled end faces 466, 476, exterior cover 465 may impart torque onto end cap 475 during rotation of the exterior cover in such arrangements.

Figure 7A:
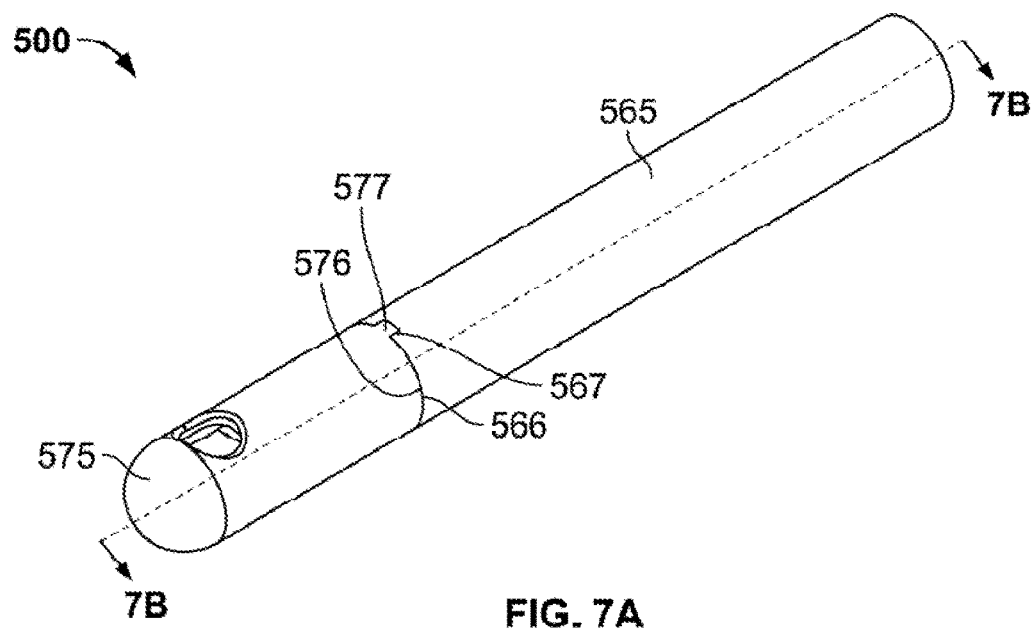
FIG. 7A is a perspective view of an optical probe in accordance with another embodiment.
Figure 7B:
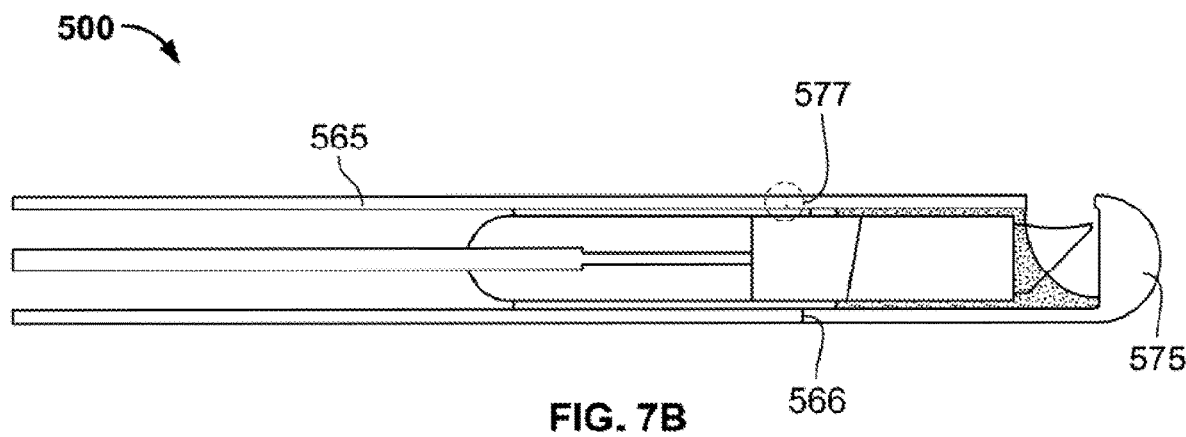
FIG. 7B is a cross-sectional view of the optical probe of FIG. 7A along the lines 7B-7B.

As shown in FIGS. 7A and 7B, optical probe 500 may be substantially the same as optical probe 400 with the exception that optical probe 500 may include exterior cover 565 and end cap 575 in place of exterior cover 465 and end cap 475, respectively. Exterior cover 565 may be substantially the same as exterior cover 465 with the exception that exterior cover 565 may include end face 566 defining groove 567 in place of end face 466. End cap 575 may be substantially the same as end cap 475 with the exception that end cap 575 may have end face 576 in place of end face 576 in which end face 576 may include key 577 which may be received in groove 567 of end face 466 of exterior cover 565. In this manner, exterior cover 565 may impart torque onto end cap 575 during rotation of the exterior cover.

Figure 8A:
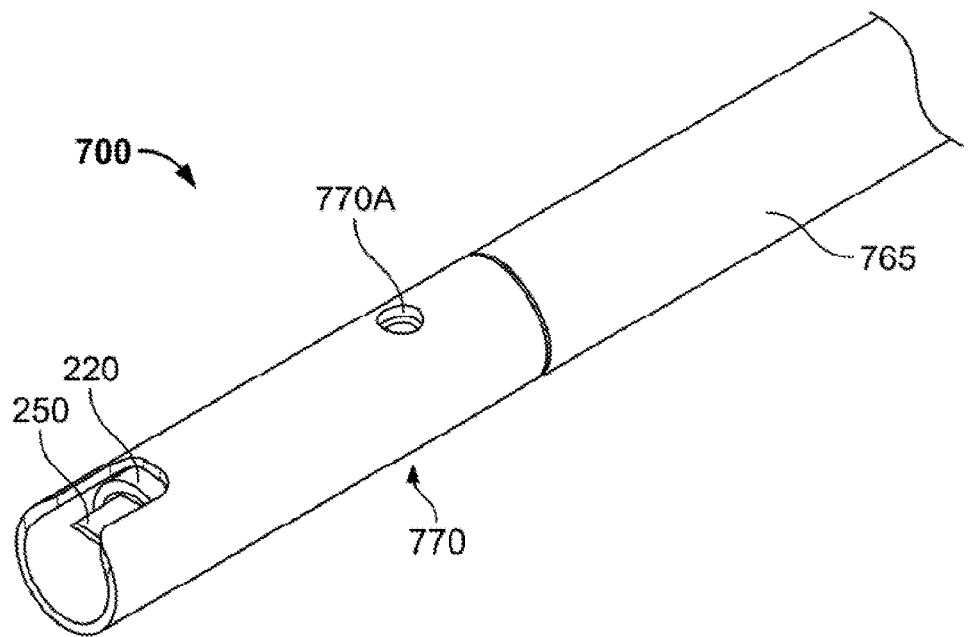
FIG. 8A is a perspective view of an optical probe in accordance with another embodiment.
Figure 8B:
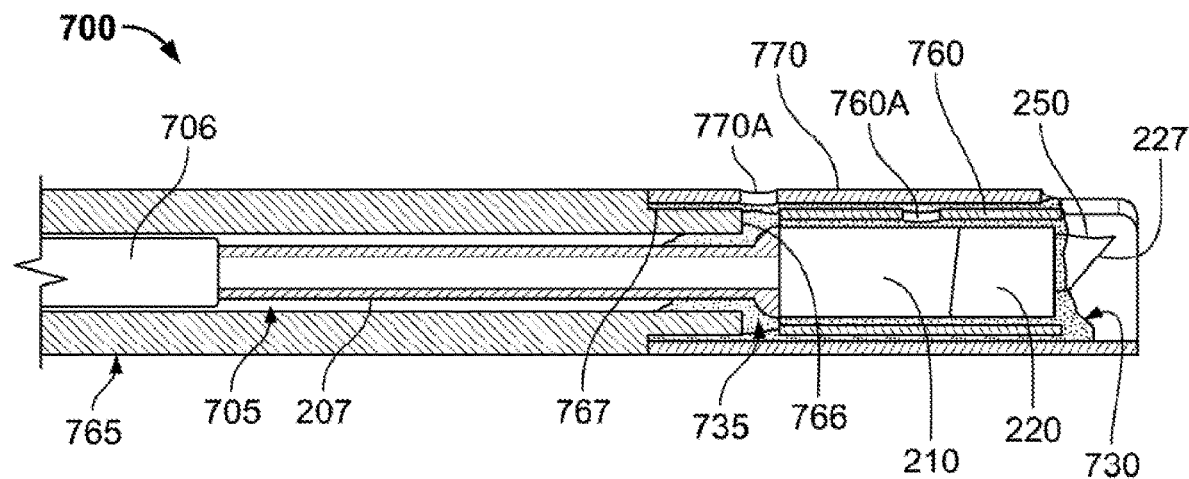
FIG. 8B is a cross-sectional view of the optical probe of FIG. 8A along the lines 8B-8B.

As shown in FIGS. 8A and 8B, optical probe 700 may be substantially the same as optical probe 200 with the exception that optical probe 700 may not include potting 209 and end cap 275, may include a combination of inner cover 760 and outer cover 770 in place of a combination of inner cover 260, end cap 275 and outer cover 270, exterior cover 765 in place of exterior cover 265, optical fiber 705 in place of optical fiber 205, and first adhesive 730 in place of adhesive 230, and additionally may include second adhesive 735. Inner cover 760 may be substantially the same as inner cover 260 with the exception that inner cover 760 may act as a sleeve extending around and only along spacer 210 and first optical component 220. Like inner cover 260, inner cover 760 may extend distally beyond first optical component 220. Outer cover 770 may extend along and directly cover a distal portion of exterior cover 765, directly cover a portion of optical fiber 705 (without jacket 706) with the exception of adhesive that may be applied between the outer cover and the optical fiber as discussed further herein, directly cover the entirety of inner cover 760, and directly cover second optical component 250. In this manner, outer cover 770 may be the outermost component at the distal end of optical probe 700 in which the outer cover may cover a majority of the end of optical probe 700. As shown, outer cover 770 may define an opening at its distal end such that, in contrast to optical probe 200, optical probe 700 may be exposed to its surroundings. In this manner, inner cover 760, a combination of the inner cover, spacer 210 and first optical component 220, or a combination of the inner cover, the spacer, the first optical component, and second optical component 250 may be inserted through the opening defined at the distal end of the outer cover. Exterior cover 765 may be substantially the same as exterior cover 265 with the exception that exterior cover 765 may have a distal end face 766 that circumferentially surrounds optical fiber 705 (without jacket 706). Exterior cover 765 may define step 767 at its distal end in which outer cover 770 extends over the step such that the exterior cover and the outer cover form a continuous, uninterrupted outer surface of optical probe 700.

In some arrangements, as shown in FIG. 8B, first adhesive 730, which may be but is not limited to being an epoxy, urethane, or acrylic adhesive, may be applied to the same region adjacent to first optical component 220 and second optical component 250 but may also be further applied distally and generally below angled surface 227, which may be coated with reflective coating 231 (see FIG. 4B), of second optical component 250 and may also be applied, as shown, to extend proximally. In this manner, first adhesive 730 may any of or, as shown, all of attach inner cover 760 to spacer 210 and first optical component 220, attach outer cover 770 to inner cover 760, and attach outer cover 770 to exterior cover 765. Still referring to FIG. 8B, optical fiber 705 (without jacket 706) may be directly attached to spacer 210, or the first optical component 220 in some alternative arrangements without the spacer, and may have a thickness such that outer cover 770 is spaced apart from an exposed surface of the optical fiber to form a gap defined by the exposed surface of the optical fiber, the outer cover, the spacer (or alternatively the first optical component), and exterior cover 765. In this manner, this gap, which initially during fabrication is an air gap, allows for variation in either or both of the concentricity of optical fiber 705 and spacer 210 and the diameters of the optical fiber and the spacer.

As shown, the entirety of this gap may be filled with second adhesive 735, which may be but is not limited to being an epoxy, urethane, or acrylic adhesive, or in alternative arrangements a resilient filling material, e.g. a resilient polymer, with the exception that first adhesive 730 may be applied between the second adhesive and outer cover 770. As in this example, second adhesive 735 or the resilient filling material may be softer, i.e., more compressible, than first adhesive 730. Use of adhesive in the gap may provide support for optical fiber 705 during rotation of optical probe 700. In alternative arrangements, the entirety of the gap may be filled with second adhesive 735 or the resilient filling material, or the entirety of the gap may be filled with first adhesive 730. In still other arrangements, the gap may not be filled at all such that the gap remains as an air gap. In this manner, stresses that may be caused by uneven forces acting at various regions along the interface of optical fiber 205 and first adhesive 730 due to the filling of the gap when using second adhesive 735, or the resilient filling material, may be avoided.

With reference to FIG. 8B, in fabricating optical probe 700, a distal portion of optical fiber 705 after stripping fiber jacket 706 away from a portion of the optical fiber may be attached by an adhesive or otherwise fused to a proximal end of spacer 210. For example, a distal end of optical fiber 705 preferably may be fused to the proximal end of spacer 210 by welding or other high heating method. In another example, a material such as an adhesive may be applied around a circumference of optical fiber 705 and to spacer 210 in which the adhesive may also be applied between the distal end of the optical fiber and the spacer or in which an anti-reflective coating may be applied to either or both of the distal end of the optical fiber and the spacer. Next, either first optical component 220 may be attached by an adhesive or otherwise fused, such as by welding or other high heating method to spacer 210 or to second optical component 250. Exterior cover 765 then may be slid over stripped and unstripped portions of optical fiber 705. Next, inner cover 760 may be slid proximally over attached spacer 210 and first optical component 220, which in some arrangements may have an adhesive such as first adhesive 730 pre-applied to either or both of their surfaces, such that a proximal end of the inner cover is in alignment with spacer 210. An amount of first adhesive 730, which may only be a drop, may be applied to either spacer 210 or first optical component 220 through hole 760A of inner cover 760, in the example shown spacer 210. Additional first adhesive 730 may then be applied onto any of or all of an outer surface of inner cover 760, step 767 of exterior cover 765, and an inner surface of outer cover 770. First adhesive 730 may be attached to second optical component 250 such that the first adhesive circumferentially surrounds an edge of the second optical component surrounding the second end surface of the second optical component. In this manner, space between inner cover 760 and the edge of second optical component 250 in a radial direction from the edge to the inner cover may be removed. Outer cover 770 then may be slid proximally over inner cover 760 and onto step 767 of exterior cover 765, although in alternative arrangements the outer cover and the inner cover may be formed as an integral, monolithic component in the same form as the combination of outer cover 770 and inner cover 760 shown in FIGS. 8A and 8B such that the component has various stepped regions. Outer cover 770 may include hole 770A in which the outer cover preferably may be positioned such that the hole is positioned axially between a distal end of exterior cover 765 and a proximal end of inner cover 760. In this manner, step 767 of exterior cover 765 may be sized such that a proximal portion of outer cover 770 proximal to hole 770A of the outer cover may be extend over the step of the exterior cover such that the exterior cover and the outer cover form a continuous, uninterrupted outer surface of optical probe 700.

Additional first adhesive 730 or preferably second adhesive 735 may be applied through hole 770A and into the gap defined by defined by the exposed surface of optical fiber 705, outer cover 770, first optical component 220, and exterior cover 765. In alternative arrangements of optical probe 700 without either or both of hole 760A of inner cover 760 and hole 770A of outer cover 770, adhesive may be applied, respectively, to the combination of spacer 210 and first optical component 220 and to the gap defined by the exposed surface of optical fiber 705, outer cover 770, first optical component 220, and exterior cover 765.

In some arrangements, outer cover 770 may be but is not limited to being made of metals, such as stainless steel, and various polymers, such as but not limited to polyimide. When made of stainless steel or polyimide, outer cover 770 may be machined into a desired form, such as that best shown in FIG. 8A. In some arrangements, outer cover 770 may be molded over exterior cover 765. In some such arrangements, outer cover 770 and inner cover 760 may be a monolithic component in the form of a single continuous molded part and further may be in the same form as the combination of outer cover 770 and inner cover 760 shown in FIGS. 8A and 8B. In some alternative arrangements, such as for relatively low rotational speeds which preferably may be less than or approximately equal to 3000 rpm, the outer cover may abut the distal end of the exterior cover instead of overlapping with the exterior cover.

Figure 9:
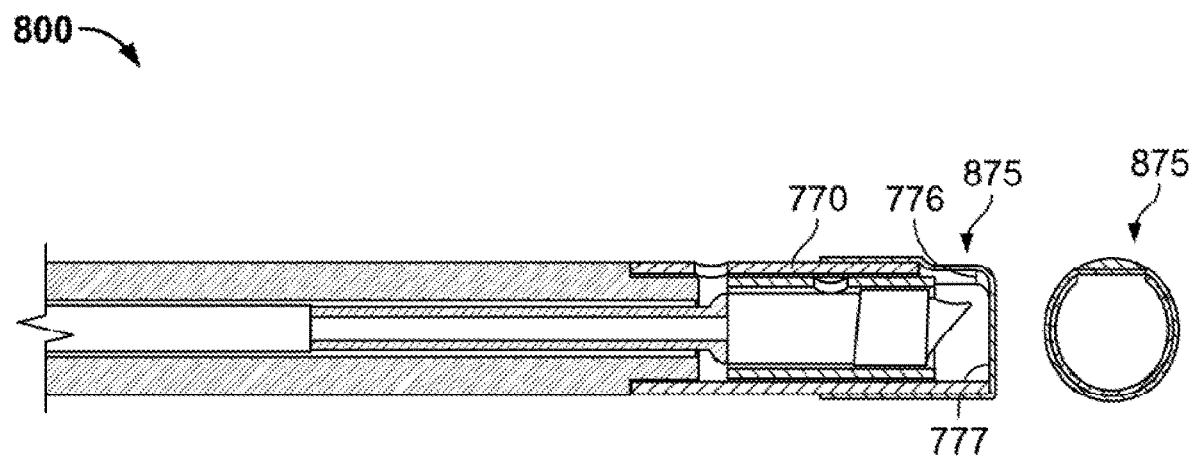
FIG. 9 shows cross-sectional side views of an optical probe in accordance with another embodiment.

Referring now to FIG. 9, optical probe 800 may be substantially the same as optical probe 700 with the exception that optical probe 800 may further include end cap 875. In such an arrangement, end cap 875 may be attached to the distal end of optical probe 700. As shown, end cap 875 may be applied in the form of a transparent thin sheath that may circumferentially surround a distal portion and the distal end of outer cover 770. As in this example, end cap 875 may be but is not limited to being made of polyethylene terephthalate (PET) or other plastics that may be liquid-resistant, and in some instances moisture resistant, up to a highest pressure experienced in the bloodstream of a human or other living being, as appropriate. During fabrication of optical probe 700, optical probe 800 may be formed by applying PET resin around a distal portion and over the distal end of outer cover 770. The PET resin may then be cured through the application of heat to optical probe 700. In this manner, the PET resin may harden and shrink. As shown, in shrinking, the cured PET resin may form flat sections in regions in which the resin is applied over holes or openings, e.g., over distal opening 777 defined by the distal end of outer cover 770 or over side opening 776 of outer cover 770. The thickness of end cap 875 may be in the range of preferably approximately 5 µm to approximately 50 µm, and more preferably approximately 10 µm. In this manner, liquid materials, and in some instances moisture, may be prevented from entering into outer cover 770 through distal opening 777 or side opening 776 while at the same time interference on light emissions through end cap 875 may be minimized.

Figure 10:
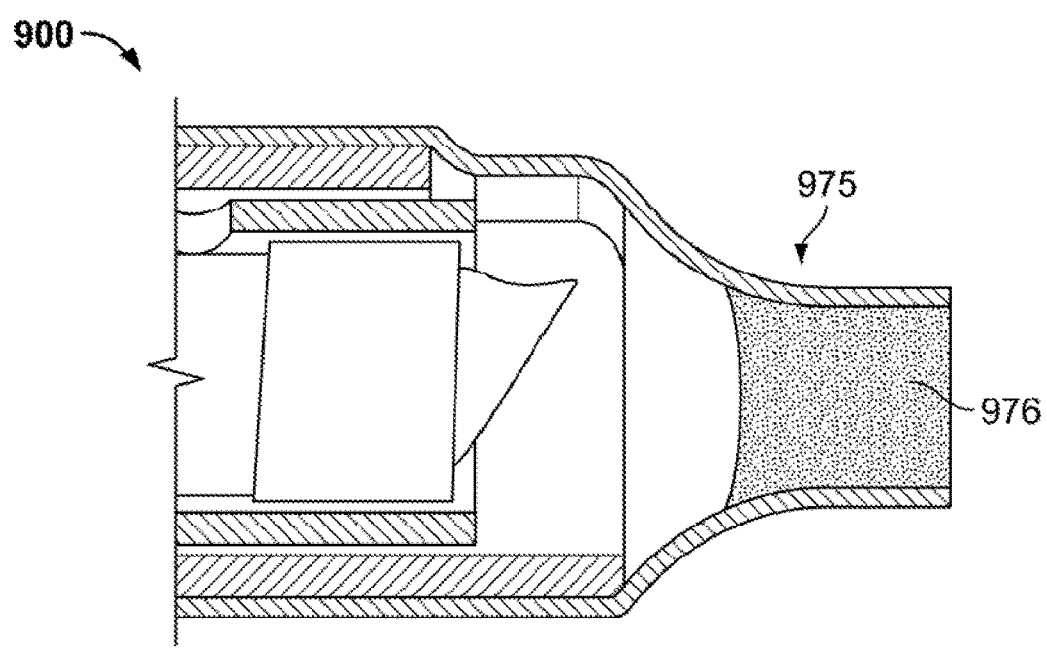
FIG. 10 is a cross-sectional view of a distal portion of an optical probe in accordance with another embodiment.

As shown in FIG. 10, optical probe 900 may be substantially the same as optical probe 800 with the exception that optical probe 900 may include end cap 975 in place of end cap 875. End cap 975 may be substantially the same as end cap 875 with the exception that a distal portion of end cap 975 may be in the form of a tube. As shown, the tubular portion of end cap 975 may neck down in a distal direction. In such arrangements, adhesive 976, which may be but is not limited to being an epoxy, urethane, or acrylic adhesive, may be applied into a distal end of end cap 975 such that the adhesive provides a complete barrier to liquids entering the end cap. In this manner, end cap 975 may provide a stronger barrier configured to withstand greater compression forces at the distal end of optical probe 900 relative to end cap 875 of optical probe 800.

Figure 11A:
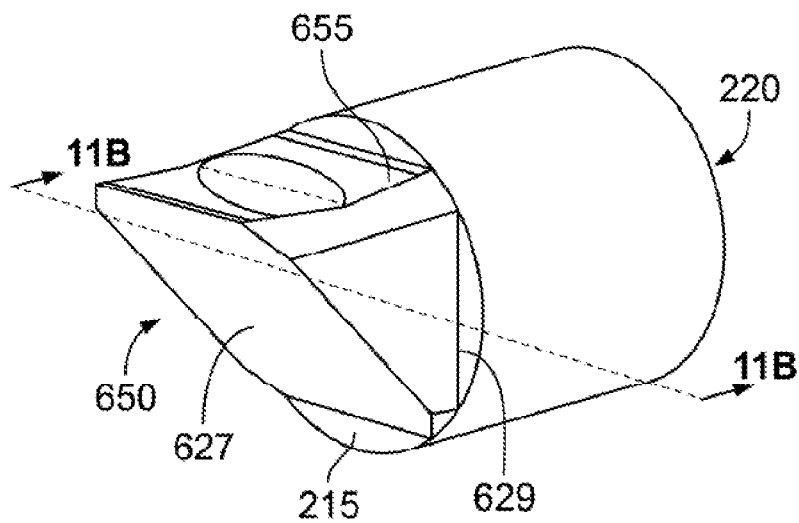
FIG. 11A is a perspective view of an optical component assembly in accordance with another embodiment.
Figure 11B:
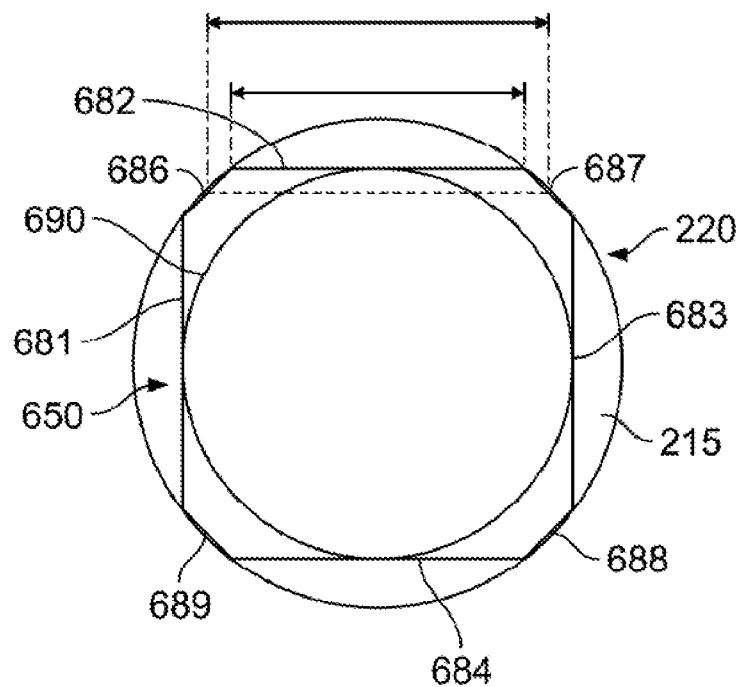
FIG. 11B is a cross-sectional view of the optical component assembly of FIG. 8A along the lines 8B-8B.

Referring now to FIGS. 11A and 11B, second optical component 650 may be attached to first optical component 220 as shown and may be used in place of second optical component 250. Second optical component 650 may be substantially the same as optical component 150 with the exception that second optical component 650 may have a truncated planar surface 629, a truncated planar (angled) surface 627, and a truncated concave exit surface 655 in place of planar surface 29, planar surface 27, and concave surface 155 of optical component 150 and further may have a larger perimeter than optical component 150 about an axis extending in a direction perpendicular to truncated planar surface 629 and passing through truncated planar surface 627. Truncated planar surface 629 may include four primary edges 681-684 and four secondary edges 686-689 extending between pairs of each of the primary edges. In the arrangement shown, the four primary edges 681-684 are of equal size and the four secondary edges 686-689 are of equal size, although in alternative arrangements, these edges may have different sizes from at least some of their counterpart edges. Ends of each of the four secondary edges 686-689 may confront points on the outer diameter of first optical component 220 when second optical component 650 is properly aligned with the first optical component, such that the entirety of a profile of second optical component 650 lies within optical interface surface 215 of the first optical component. In this manner, a larger aperture, as depicted by inscribed circle 690, is formed by truncated planar surface 629 of second optical component 650 than is provided by planar surface 29 of optical component 150. As a result, more light from first optical component 220 may enter second optical component 650 at planar surface 629 than may enter at surface 29 of optical component 150. Desirably, the truncated exit surface 655 may have a predetermined truncated configuration relative to concave surface 155 of optical component 150, the truncated angled surface 627 may have a predetermined truncated configuration relative to angled surface 27, and exit surface 655 may have a predetermined concave configuration, to provide that all or substantially all of the light entering at planar surface 629 exits the second optical component 650 at exit surface 655 and to maximize the amount of light exiting the second optical component that enters the second optical component at planar surface 629.

During use, optical probe 200, 300, 400, 500, 700, 800, 900 or any such optical probe using second optical component 650 in place of second optical component 250, may be used to illuminate objects or structures. In some arrangements, optical probe 200 may be used for certain medical procedures, including for illuminating internal body structures, such as may be needed for optical coherence tomography (OCT) or other medical imaging techniques, during minimally invasive surgical procedures. During such procedures, optical probe 200, 300, 400, 500, 700, 800, 900 may be moved along internal body structures, e.g., a blood vessel, through a catheter, which may be catheter tubing, preferably without friction with the catheter and caused to be rotated by way of a rotary joint or other mechanical connection. Optical probe 200, 300, 400, 500, 700, 800, 900 may be configured such that the spot size of a light beam emitted from the probe may correspond with the structures that are desired to be illuminated. In one arrangement, the light beam emitted from probe 200, 300, 400, 500, 700, 800, 900 may be elliptical and have a spot size of approximately between 5 and 100 μm. In an embodiment, probe 200, 300, 400, 500, 700, 800, 900 may be configured such that the spot size of the emitted light beam facilitates the illumination and identification of particular cells, e.g., cancer cells.

Figure 12:
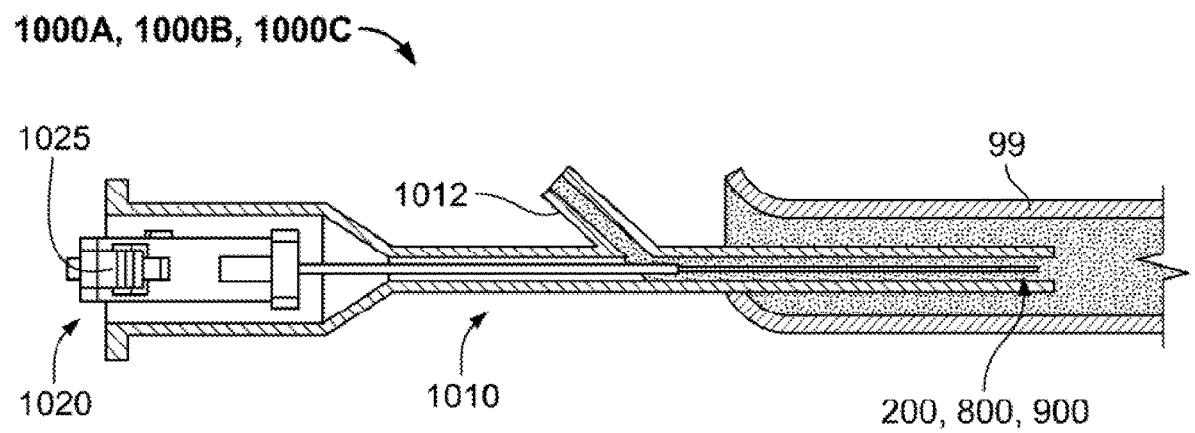
FIGS. 12 and 13 are cross-sectional views of portions of respective optical systems in use in a patient's vascular system.

With reference to FIG. 12, in one example, optical probe 200, 800, 900 may be part of respective optical system 1000A, 1000B, 1000C in which the respective optical probe may be inserted into a tube of catheter 1010 and in which the respective optical probe may be attached to connector and motor assembly 1020. Connector and motor assembly 1020 may include optical connector 1025 for transmitting a light beam to respective optical probe 200, 800, 900. Connector and motor assembly 1020 may further supply a rotational force to exterior cover 765 to cause a rotation of attached second optical component 250, 650. In this manner, in the example optical probe 200, 800, 900 may facilitate illumination of artery 99 to identify abnormalities of the artery as discussed above. Optical probe 200 includes outer cover 270 and optical probe 800, 900 includes respective end cap 875, 975 such that the optical probe may operate in a liquid or otherwise moist environment such as in the example shown in which flushing liquid is added into catheter 1010 through side tube 1012 of the catheter.

Figure 13:
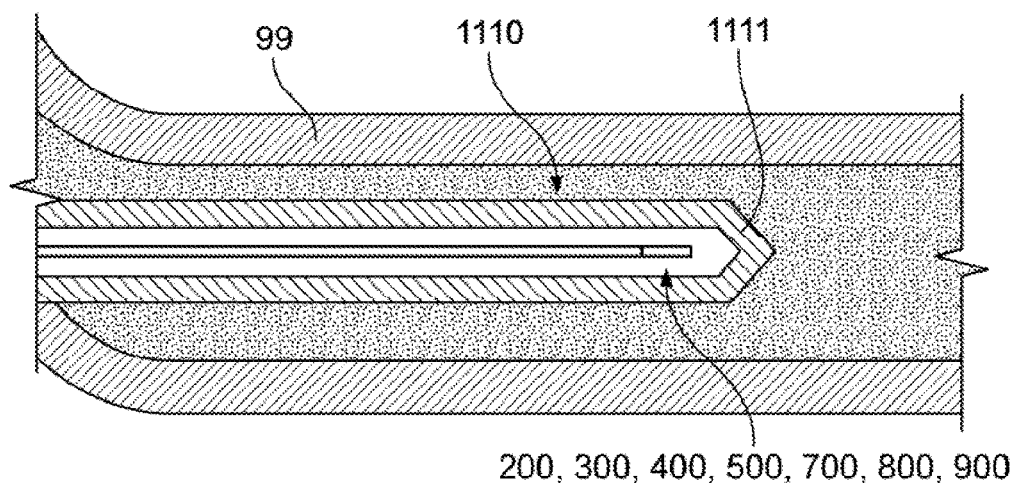

Referring now to FIG. 13, in another example, optical probe 200, 300, 400, 500, 700, 800, 900 may be part of another optical system substantially similar to optical system 1000A, 1000B, 1000C with the exception that this alternative system may include catheter 1110 in place of catheter 1010. Catheter 1110 may be substantially the same as catheter 1010 with the exception that catheter 1110 includes tip 1111, which as shown may be pointed, that separates the optical system from the liquid or otherwise moist surroundings of artery 99 exterior to the catheter and generally does not include a side tube such as side tube 1012 of catheter 1010.

It is to be further understood that the disclosure set forth herein includes any possible combinations of the particular features set forth above, whether specifically disclosed herein or not. For example, where a particular feature is disclosed in the context of a particular aspect, arrangement, configuration, or embodiment, that feature can also be used, to the extent possible, in combination with and/or in the context of other particular aspects, arrangements, configurations, and embodiments of the technology, and in the technology generally.

Furthermore, although the technology herein has been described with reference to particular embodiments, it is to be understood that these embodiments are merely illustrative of the principles and applications of the present technology. It is therefore to be understood that numerous modifications may be made to the illustrative embodiments and that other arrangements may be devised without departing from the spirit and scope of the present technology. In this regard, the present technology encompasses numerous additional features in addition to those specific features set forth in the claims below. Moreover, the foregoing disclosure should be taken by way of illustration rather than by way of limitation as the present technology is defined by the appended claims.

The invention claimed is:

1. An optical probe comprising:
an optical fiber assembly including an optical fiber;
an optical component assembly including a first optical component having a first end surface and a second optical component having a second end surface confronting the first end surface of the first optical component, wherein the second end surface of the second optical component is attached to the first end surface of the first optical component;
a spacer attached to the first optical component; and
a first cover attached to and circumferentially surrounding the optical fiber assembly, wherein a first material or a second material different from the first adhesive attaches the first optical component to the first cover,
wherein the first material is attached to the second optical component such that the first material circumferentially surrounds an edge of the second optical component surrounding the second end surface of the second optical component and thereby removes any space between the first cover and the edge of the second optical component in a radial direction from the edge of the second optical component to the first cover,
wherein an end of the optical fiber is fused to the spacer and is surrounded by a coating, and
wherein the first optical component and the second optical component are configured such that a light beam exiting the first optical component at the first end surface enters the second optical component at the second end surface, and wherein the second optical component further comprises:
a generally planar angled surface, wherein the second end surface is arranged at a predetermined angle relative to the angled surface such that a light beam that enters the second optical component at the second end surface is reflected at the angled surface; and
an exit surface arranged such that light reflected by the angled surface is directed towards the exit surface.

2. The optical probe of claim 1, wherein
the first material is a first adhesive,
the second material is a second adhesive, and
the one of the first adhesive or the second adhesive that attaches the first optical component to the first cover is bounded by the first cover.

3. The optical probe of claim 1, wherein the exit surface of the second optical component is a concave surface curving inwardly towards an interior of the second optical component.

4. The optical probe of claim 1, wherein the first optical component is a GRIN lens and the spacer is a glass spacer rod, the glass spacer rod being positioned within the first cover.

5. The optical probe of claim 1, further comprising a sheath, wherein the optical fiber defines a longitudinal axis, wherein the first cover defines an opening radially offset from the longitudinal axis and overlying the exit surface of the second optical component, and wherein the sheath covers the opening.

6. The optical probe of claim 5, wherein at least a portion of the sheath covering the opening is flat.

7. The optical probe of claim 1, further comprising a second cover overlapping or underlapping the first cover.

8. The optical probe of claim 7, wherein the second cover is a torque coil configured to exert torque on the optical probe such that the second optical component is rotated about a longitudinal axis defined by the optical fiber.

9. The optical probe of claim 7, wherein the optical fiber defines a longitudinal axis, and wherein the second cover is configured to cover a terminal end of the optical probe to prevent exposure of the second optical component at the terminal end, the longitudinal axis of the optical fiber passing through the second cover.

10. The optical probe of claim 7, wherein the optical fiber is attached to the spacer such that the first cover is spaced apart from an exposed surface of the optical fiber to form a gap therebetween, the gap being defined by at least the exposed surface of the optical fiber, the first cover, and the spacer.

11. The optical probe of claim 10, wherein the first cover includes an inner sleeve and an outer sleeve attached by a third material to and circumferentially surrounding the inner sleeve, wherein the inner sleeve is attached by the third material to the first optical component, and wherein the gap is filled with the third material.

12. The optical probe of claim 1, wherein the first cover includes an inner sleeve and an outer sleeve attached to and circumferentially surrounding the inner sleeve.

13. The optical probe of claim 12, wherein the first cover further includes a torque coil attached to the outer sleeve, the torque coil being configured to exert torque on the optical probe.

14. The optical probe of claim 1, wherein the optical fiber is attached to the spacer such that the first cover is spaced apart from an exposed surface of the optical fiber to form a gap therebetween, the gap being defined by at least the exposed surface of the optical fiber, the first cover, and the spacer.

15. The optical probe of claim 14, wherein the first cover includes an inner sleeve and an outer sleeve attached by a third material to and circumferentially surrounding the inner sleeve, wherein the inner sleeve is attached by the third material to the first optical component, and wherein the gap is filled with the third material.

16. The optical probe of claim 15, wherein
the first material is a first adhesive,
the second material is a second adhesive,
the third material is a third adhesive,
the first adhesive and the third adhesive are the same adhesive, and
the second adhesive is different from the third adhesive.

17. The optical probe of claim 1, wherein material including the first material extends between and is bounded by the first cover and the second optical component.

18. The optical probe of claim 1, wherein the coating is epoxy, urethane, acrylic, or polyimide.

19. An optical probe comprising:
an optical fiber assembly including an optical fiber;
an optical component assembly including a first optical component having a first end surface and a second optical component having a second end surface confronting the first end surface of the first optical component, wherein the second end surface of the second optical component is attached to the first end surface of the first optical component;
a first cover attached to and circumferentially surrounding the optical fiber assembly, wherein a first adhesive or a second adhesive different from the first adhesive attaches the first optical component to the first cover,
wherein the first adhesive is attached to the second optical component such that the first adhesive circumferentially surrounds the second end surface of the second optical component, the first cover being attached to the second optical component by adhesive including the first adhesive, and
wherein the first optical component and the second optical component are configured such that a light beam exiting the first optical component at the first end surface enters the second optical component at the second end surface, and wherein the second optical component further comprises:
a generally planar angled surface, wherein the second end surface is arranged at a predetermined angle relative to the angled surface such that a light beam that enters the second optical component at the second end surface is reflected at the angled surface; and
an exit surface arranged such that light reflected by the angled surface is directed towards the exit surface.

20. The optical probe of claim 19, further comprising a spacer attached to the first optical component, wherein the optical fiber is fused to the spacer and is surrounded by a coating.

21. The optical probe of claim 19, wherein the adhesive that includes the first adhesive extends between and is bounded by the first cover and the second optical component without covering an entirety of the second optical component.

22. The optical probe of claim 19, wherein the first cover includes an inner sleeve and an outer sleeve attached to and circumferentially surrounding the inner sleeve.

* * * * *